United States Patent
Dotan et al.

(10) Patent No.: US 8,216,791 B2
(45) Date of Patent: *Jul. 10, 2012

(54) METHOD FOR DIAGNOSING MULTIPLE SCLEROSIS

(75) Inventors: Nir Dotan, Shoham (IL); Avinoam Dukler, Moddi'in (IL)

(73) Assignee: Glycominds Ltd., Modi'in (IL)

( * ) Notice: Subject to any disclaimer, the term of this patent is extended or adjusted under 35 U.S.C. 154(b) by 267 days.

This patent is subject to a terminal disclaimer.

(21) Appl. No.: 12/556,296

(22) Filed: Sep. 9, 2009

(65) Prior Publication Data

US 2010/0159472 A1    Jun. 24, 2010

Related U.S. Application Data

(63) Continuation-in-part of application No. 11/345,190, filed on Jan. 31, 2006, now Pat. No. 7,906,291, which is a continuation-in-part of application No. 11/047,124, filed on Jan. 31, 2005, now Pat. No. 7,575,592.

(51) Int. Cl.
    *G01N 33/53* (2006.01)
(52) U.S. Cl. ......................................... 435/7.1
(58) Field of Classification Search .................. None
    See application file for complete search history.

(56) References Cited

U.S. PATENT DOCUMENTS

| | | | |
|---|---|---|---|
| 5,030,560 A | 7/1991 | Sinor et al. | 435/7.21 |
| 6,972,172 B2 | 12/2005 | Dukler et al. | 435/6 |
| 7,537,900 B2 | 5/2009 | Dotan et al. | 435/7.1 |
| 7,572,592 B2 | 8/2009 | Dotan et al. | |
| 2004/0077023 A1 | 4/2004 | Dotan et al. | 435/7.2 |
| 2004/0241763 A1 | 12/2004 | Dotan et al. | 435/7.2 |
| 2006/0172338 A1 | 8/2006 | Dotan et al. | 435/7.1 |
| 2006/0234301 A1 | 10/2006 | Dotan et al. | |

FOREIGN PATENT DOCUMENTS

| | | |
|---|---|---|
| WO | WO 00/49412 | 8/2000 |
| WO | WO 01/14881 A1 | 3/2001 |
| WO | WO 01/51207 A1 | 7/2001 |
| WO | WO-0151207 A1 | 7/2001 |
| WO | WO 02/18950 A1 | 3/2002 |
| WO | WO 02/064556 A2 | 8/2002 |
| WO | WO 03/000733 A2 | 1/2003 |
| WO | WO 2004/015420 A1 | 2/2004 |
| WO | WO-2004034031 A2 | 4/2004 |
| WO | WO-2006/117689 A2 | 11/2006 |

OTHER PUBLICATIONS

Bao *J. Chromatogr. B.*, 699(1+2):463-480 (1997).
Berger et al. *N. Engl. J. Med.*, 349:139-145 (2003).
Bozzaro et al. *Cell Differentiation*, 17:83-94 (1985).
Brex et al. *N. Engl. J. Med.*, 346(3):158-164 (2002).
Carotenuto et al. *J. Med. Chem.*, 44:2378-2381 (2001).
Comi et al. *Lancet*, 357:1576-1582 (2001).
Holme et al. *Carbohydr. Res.*, 8:43-55 (1968).
Hou et al. *J. Immunol.*, 170:4373-4379 (2003).
Jacobs et al. *Ann. Neurol.*, 41(3):392-398 (1997).
Jacobs et al. *N. Engl. J. Med.*, 343(13):898-904 (2000).
Kurtzke *Neurol.*, 33(11):1444-1452 (1983).
Matsuda et al. *Mol. Immun.*, 24(5):421-425 (1987).
McDonald et al. *Ann. Neurol.*, 50(1):121-127 (2001).
O'Riordan et al. *Brain*, 121:495-503 (1998).
Papini et al. *Proceedings of the 10th International Congress of Immunology*, Monduzzi Editore, pp. 1239-1244 (1998).
Poser et al. *Ann. Neurol.*, 13(3):227-231 (1983).
Rongen et al. *J. Immunol. Meth.*, 204(2):105-133 (1997).
Saveliev et al. *Immun. Letters*, 86:291-297 (2003).
Schmalzing et al. *Electrophoresis*, 18(12-13):2184-2193 (1997).
Schwarz et al. *Glycobiol*, 13(11):749-754 (2003).
Self et al. *Curr. Opin. Biotechnol.*, 7:60-65 (1996).
Weinshenker et al. *Brain*, 112(part VI):1419-1428 (1989).
Zhan et al. *Biochem. Biophys. Res. Commun.*, 308(1):12-22 (2003).
International Search Report for PCT/IB2006/001656, mailed Nov. 8, 2006.
Mazzucco, S., et al. Bioorg. Med. Chem. Letters (1999) 9:167-172.
Patent Abstract of Japan for Japanese Laid-Open Publication No. 02-161357, published Jun. 21, 1990.
Schwarz, M., et al., J. Neuro. Sci. (2006) 244:59-68.
Alberts et al., "Sugars Are Food Molecules of the Cell", in *Molecular Biology of the Cell*, Garland Publishing Inc., New York & London, pp. 50-51 (1983).
Banin et al., "A Novel Linear Code@ Nomenclature for Complex Carbohydrates", *Trends Glycoscience Glycotech.*, 14(77):127-137 (2002).
Bergamaschi, R., "Prognostic Factors in Multiples Sclerosis", *Int. Rev. Neurobiol.*, 79:423-447 (2007).
Binder et al., "The role of natural antibodies in atherogenesis", *J. Lipid Res.*, 46:1353-1363 (2005).
Boneschi et al., "Mitoxantrone for multiple sclerosis", *Cochrane Database of Systematic Rev.*, 4:CD002127 (2005).
Brusaferri et al., "Steroids for multiple sclerosis and optic neuritis: a meta-analysis of randomized controlled clinical trials", *J. Neurol.*, 247(6):435-442 (2000).

(Continued)

*Primary Examiner* — Gerald R Ewoldt
(74) *Attorney, Agent, or Firm* — Mintz Levin Cohn Ferris Glovsky and Popeo, P.C.; Ivor R. Elrifi; Ingrid A. Beattie

(57) ABSTRACT

Disclosed is a method for diagnosing and prognosing multiple sclerosis and more particularly to a method for diagnosing and prognosing multiple sclerosis by measuring levels of antibodies. The levels of IgM-type anti-Glc($\alpha$1,2)Glc($\alpha$) or Glc($\alpha$1,3)Glc($\alpha$) or Glc($\alpha$1,6)Glc($\alpha$) antibodies in serum act as diagnostic markers for MS disease and as prognostic biomarkers for the conversion of CIS patients suggestive of MS to clinically definite MS (CDMS) within 24 months.

6 Claims, 7 Drawing Sheets

OTHER PUBLICATIONS

Confavreux et al., "Early clinical predictors and progression of irreversible disability in multiple sclerosis: an amnesic process", *Brain*, 126:770-782 (2003).
Dovio et al., "Immediate Fall of Bone Formation and Transient Increase of Bone Resorption in the Course of High-Dose, Short-Term Glucocorticoid Therapy in Young Patients with Multiple Sclerosis", *Clin. Endocrinol, Metab.*, 89(10):4923-4928 (2004).
Felici et al., "Phage-Displayed Peptides as Tools for Characterization of Human Sera", *Meth. Enzymol.*, 267:116-129 (1996).
Fisniku et al., "Disability and $T_2$ MRI lesions: a 20-year follow-up of patients with relapse onset of multiple sclerosis", *Brain*, 131:808-817 (2008).
Freedman et al., "Anti-α-glucose-based glycan IgM antibodies predict relapse activity in multiple sclerosis after the first neurological event", *Multiple Sclerosis*, 15(4):422-430 (2009).
Freedman et al., "Recommended Standard of Cerebrospinal Fluid Analysis in the Diagnosis of Multiple Sclerosis", *Arch. Neurol.*, 62:865-870 (2005).
Gonsette, R.E., "Compared benefit of approved and experimental immunosuppressive therapeutic approaches in multiple sclerosis", *Exp. Opin. Pharmacother.*, 8(8):1103-1116 (2007).
Gyorgy et al., "Natural autoantibodies reactive with glycosaminoglycans in rheumatoid arthritis", *Arthritis Res. Ther.*, 10(5):1-12 (2008).
Johnson, K.P., "Control of multiple sclerosis relapses with immunomodulating agents", *J. Neurol. Sci.*, 256:(1):S23-S28 (2007).
Kappos et al., "Effect of early versus delayed interferon beta-1b treatment on disability after a first clinical event suggestive of multiple sclerosis: a 3-year follow-up analysis of the Benefit study", *Lancet*, 370(9585):389-397 (2007).
Kuhle et al., "Lack of Association between Antimyelin Antibodies and Progression to Multiple Sclerosis", *N. Engl. J. Med.*, 356:371-378 (2007).
Leary et al., "Primary Progressive Multiple Sclerosis Current and Future Treatment Options", *CNS Drugs*, 19(5):369-376 (2005).
Lolli et al., "An N-glucosylated peptide detecting disease-specific autoantibodies, biomarkers of multiple sclerosis", *Proc. Natl. Acad. Sci. U.S.A.*, 102(29):10273-10278 (2005).
Lolli et al., "The glycopeptides CSF114(Glc) detects serum antibodies in multiple sclerosis", *J. Neuroimmunol.*, 167:131-137 (2005).
Mandrioli et al., "A multifactorial prognostic index in multiple sclerosis", *J. Neurol.*, 255:1023-1031 (2008).
Martinelli et al., "Mitoxantrone for multiple sclerosis", *Cochrane Database System Reviews*, (4):CD002127 (2005).
Miller et al., "Biomarkers and Surrogate Outcomes in Neurodegenerative Disease: Lessons from Multiple Sclerosis", *NeuroRx*, 1:284-294 (2004).
Miller et al., "Differential diagnosis of suspected multiple sclerosis: a consensus approach", *Multiple Sclerosis*, 14:1157-1174 (2008).
Munari et al., "Therapy with glatiramer acetate for multiple sclerosis", *Cochrane Database of Systematic Rev.*, 4:CD004678 (2003).
Murray, T.J., "The cardiac effects of mitoxantrone: do the benefits in multiple sclerosis outweigh the risks?", *Exp. Opin. Drug Safety*, 5(2):265-274 (2006).
Perrin et al., "A National Survey of Physician Perspectives of the Unmet Needs in the Treatment of Multiple Sclerosis", *JMCP*, 15(7):572-573 (2009) (Abstract Only).
Pirko et al., "A human antibody that promotes remyelination enters the CNS and decreases lesion load as detected by T2-weighted spinal cord MRI in a virus-induced murine model of MS", *FASEB J.*, 18:1577-1579 (2004).
Pittock et al., "Clinical Implications of Benign Multiple Sclerosis: A 20-Year Population-Based Follow-up Study", *Ann. Neuro.*, 56:303-306 (2004).
Polman et al., "Diagnostic Criteria for Multiple Sclerosis: 2005 Revisions to the McDonald Criteria", *Ann. Neurol.*, 58:840-846 (2005).
Rice et al., "Interferon in relapsing-remitting multiple sclerosis", *Cochrane Database of Systematic Rev.*, 4:CD002002 (2001).
Ritchie et al., "Reference Distributions for Immunoglobulins A, G, and M: A Practical, Simple, and Clinically Relevant Approach in Large Cohort", *J. Clin. Lab. Anal.*, 12:363-370 (1998).
Rudick et al., "Current approaches to the identification and management of breakthrough disease in patients with multiple sclerosis", *Lancet Neurol.*, 8:545-559 (2009).
Ruggieri et al., "Glatiramer Acetate in Multiple Sclerosis: A Review", *CNS Drug Rev.*, 13(2):178-191 (2007).
Simone et al., "Course and prognosis in early-onset MS. Comparison with adult-onset forms", *Neurol.*, 59(12):1922-1928 (2002).
Steinman et al., "Multiple sclerosis: a two-stage disease", *Nature Immunol.*, 2(9):762-764 (2001).
Stryer, L., *Biochemistry*, 4$^{th}$ Edition, W.H. Freeman and Company, New York, NY, pp. 472-473 (1995).
Tintore et al., "Baseline MRI predicts future attacks and disability in clinically isolated syndromes", *Neurol.*, 67:968-972 (2006).
Uttner et al., "Reversible impaired memory induced by pulsed methylprednisolone in patients with MS", *Neurol.*, 64(11):1971-1973 (2005).
van Horssen et al., "Extensive extracellular matrix depositions in active multiple sclerosis lesions", *Neurobiol. Dis.*, 24:484-491 (2006).
Vollmer, T., "The natural history of relapses in multiple sclerosis", *J. Neurol. Sci.*, 256(Suppl. 1):S5-S13 (2007).
Warrington et al., "A Recombinant Human IgM Promotes Myelin Repair After a Single, Very Low Dose", *J. Neurosci. Res.*, 85:967-976 (2007).
Yarden and Dotan, "Anti-Collagen IV IgM and anti-Glc(a1,2)Gal(b) (GAAB) IgM can be used for differentiation between Relapsing Remitting Multiple sclerosis (RRMS) patients and patients having other neurological diseases (OND)", Jul. 1, 2009.
Dalton et al., "Application of the new McDonald Criteria to Patients with Clinically Isolated Syndromes Suggestive of Multiple Sclerosis", *Ann. Neurol.*, 52:47-53 (2002).
Dotan et al., "Anti-glycan antibodies as biomarkers for diagnosis and prognosis", *Lupus*, 15(7):442-450 (2006).
Durelli et al., "MRI activity and neutralising antibody as predictors of response to interferon β treatment in multiple sclerosis", *J. Neurol. Neurosurg. Psychiatry*, 79:646-651 (2008).
Rio et al., "Relationship between MRI lesion activity and response to IFN-β in relapsing-remitting multiple sclerosis patients", *Mult. Scler.*, 14:479-484 (2008).
Sormani et al., "Modelling MRI enhancing lesion counts in multiple sclerosis using a negative binomial model: implications for clinical trials", *J. Neurol. Sci.*, 163(1):74-80 (1999).
Freedman, "Anti-alpha-glucose-based Glycan IgM Antibodies in Patients with a Clinically Isolated Syndrome: Analyses from the Betaferon in Newly Emerging Multiple Sclerosis for Initial Treatment (BENEFIT) Study", ECTRIMS, Aug. 27, 2009.

METHOD FOR DIAGNOSING MULTIPLE SCLEROSIS

RELATED APPLICATIONS

This application is a continuation-in-part of U.S. Ser. No. 11/345,190, filed Jan. 31, 2006, which is a continuation-in-part of U.S. Ser. No. 11/047,124, filed Jan. 31, 2005, now U.S. Pat. No. 7,572,592. The contents of these applications are incorporated by reference herein in their entirety.

FIELD OF THE INVENTION

The invention relates generally to a method and reagents for diagnosing, and assessing the prognosis of, multiple sclerosis and more particularly to a method and reagents for diagnosing, and assessing the prognosis of, multiple sclerosis by measuring levels of antibodies to glycans in a biological sample.

BACKGROUND OF THE INVENTION

Multiple sclerosis (MS) is a chronic autoimmune inflammatory disease of the central nervous system. It is a common cause of persistent disability in young adults. In patients suffering from MS, the immune system destroys the myelin sheet of axons in the brain and the spinal cord, causing a variety of neurological pathologies. In the most common form of MS, Relapsing-Remitting (RRMS), episodes of acute worsening of neurological function (exacerbations, attacks) are followed by partial or complete recovery periods (remissions) that are free of disease progression (stable).

About 50 percent of those patients with a clinically isolated syndrome (CIS) progress to clinically definite MS (CDMS) within 24 months of presentation (Kappos et al., 2007 Lancet, 370 (9585): 389-97).

There is a clinical need for a simple serological assay that predicts whether patients at clinically isolated syndrome (CIS) suggestive of MS will develop MS in a certain timeframe. Such a method for assisting in the diagnosis of RRMS that assesses the risk of CIS patients suggestive of MS to have a relapse within 24 months would be useful in determining treatment options for high risk CIS patients.

SUMMARY OF THE INVENTION

The invention solves a long standing problem in the field of MS—how to determine a medical treatment regimen for a subject at clinically isolated syndrome (CIS). The method involves characterizing an individual as a member of one of two groups: (i) those who are likely to progress to clinically definite multiple sclerosis (CDMS) rapidly, i.e., within 24 months, and (ii) those who are likely to progress to CDMS relatively slowly, i.e., within greater than 24 months. Segregating patients at CIS based on the relative risk of progression is a critical factor in the determination of a treatment regimen, because those in group (i) receive an aggressive disease modifying therapy (DMT) regimen, whereas those in group (ii) receive a less aggressive DMT regimen. An aggressive regimen is characterized as a higher dose, more frequent dosing, or a more potent DMT compared to the less aggressive regimen.

Dextran (P63) is a polymer of sugar units connected with one or more Glc($\alpha$1,6)Glc($\alpha$) glycosidic bonds with Glc($\alpha$1,3)Glc($\alpha$) branches. The invention is based in part on the discovery that MS patients (male or female) have higher serum levels of IgM antibodies that bind the glycan structures Glc($\alpha$1,3)Glc($\alpha$) or Glc($\alpha$1,6)Glc($\alpha$) either as a synthesized disaccharide or as a natural polymer as compared to the serum levels of these antibodies in individuals with other neurological diseases (both chronic, inflammatory or non-inflammatory). The levels of IgM-type anti-Glc($\alpha$1,2)Glc($\alpha$) or Glc($\alpha$1,3)Glc($\alpha$) or Glc($\alpha$1,6)Glc($\alpha$) antibodies in serum act as diagnostic markers for MS disease and as prognostic biomarkers for the conversion of CIS patients suggestive of MS to clinically definite MS (CDMS) within 24 months. Levels of the antibodies that predict conversion to CDMS within 24 months are used to prescribe appropriate disease modifying therapy (DMT) for CIS patients. This information is useful for patients with a normal MRI scan that would otherwise need to wait for their next MRI scan or their next clinical attack to establish or confirm a diagnosis of MS (CDMS). The information provided by the methods herein is also used to persuade CIS patients with an abnormal MRI scan to begin DMT. Some patients, i.e., those patients at high risk for conversion to CDMS, often prefer to wait until their next relapse before beginning DMT. The prognostic information from the methods described herein is useful for patients and clinicians to determine the most appropriate treatment regimen, particularly the importance of starting DMT before experiencing a second attack/relapse if conversion to CDMS is likely to occur imminently, e.g., within 24 months.

This invention describes an additional set of anti-glycan antibodies that are used to predict a second neurological attack within 24 months, or to predict disease course progression in MS. A test sample is provided from a CIS subject characterized as having suffered a first neurological event (FNE). Suitable test samples include a biological fluid selected from the group consisting of whole blood, serum, or plasma. Various anti-glycan antibodies are detected in the test sample, such as an anti-Glc ($\alpha$ 1,3) Glc ($\alpha$) antibody (GAGA3), an anti-Glc ($\alpha$ 1,6) Glc ($\alpha$) antibody (GAGA6), or an anti-glucose based polysaccharide comprising Glc ($\alpha$ 1,3) Glc ($\alpha$) and Glc ($\alpha$ 1,6) Glc ($\alpha$) disaccharides (P63). Preferably, the antibodies are IgM type antibodies.

The levels of the antibody in the test sample are not reported as a direct signal measured (e.g., fluorescence signal, optical density signal, or luminescence), but rather reported relative to a calibration sample with a predefined unit value (e.g., 50 units) that is included in each assay. The unit value of a test sample is calculated relative to the calibration sample as follows: test sample units=signal measured for test sample/signal measured for calibration sample*units of calibration sample. For example, if Enzyme linked Immune Assay (EIA) technology is used for antibodies levels and the measured signal is Optical Density (OD) in the wells, then the EIA units (EU) will be calculated as: test sample EU=OD test sample/OD calibration sample*units value of calibration sample.

The levels of the antibodies in the test sample are compared to the levels of the antibodies in a control or reference sample, wherein a higher level of the antibodies in the test sample compared to the level of the antibodies in a control sample indicates the subject has a higher risk of having a second neurological attack within 24 months.

As described in further detail below, a classification rule based on levels of sera anti-P63 IgM antibodies and patient age was developed as follows: p=1.170703−0.082399·age (years)+0.015471·anti-P63(EU). If p≧0.6114674, then the patient was classified as positive with a risk for next relapse within ≦24 months. Kaplan-Meier survival analysis indicates that patients classified as positive (above cutoff) by the classifier have a higher risk for conversion to CDMS or McDonald MS both within 24 months as compared to patients who are negative (below cutoff).

The classifier level for prediction of a relapse within 24 months in CIS patients is a control or reference level based on antibody levels and patient age, and is calculated with a formula, such as the formula above. In practice, by examining a statistically-relevant cohort of patients (e.g., 50 patients, 100 patients, etc.), a reference sera sample having an antibody level or classifier level similar to the chosen cutoff level is determined for each antibody or for the classifier level. Specifically, the reference level is determined by examining blood samples from CIS patients known to experience a second neurological attack during the twenty-four months after the first neurological attack, and from those CIS patients who did not experience a second neurological attack during the twenty-four months. A cut-off value that differentiates between the "early attack" and "late attack" patients is determined at a desired sensitivity and specificity. The control/reference sample is determined by choosing a sample with an antibody level or classifier level similar to the cut-off level.

The invention also provides methods of identifying a subject with a clinically isolated syndrome (CIS) suggestive of MS who will progress to clinically definitive multiple sclerosis (CDMS) within twenty-four months by providing a test sample from a subject and detecting in the test sample an anti-Glc ($\alpha$ 1,3) Glc ($\alpha$) antibody and an anti-Glc ($\alpha$ 1,6) Glc ($\alpha$) antibody. The levels of the antibodies in the test sample are compared to a control level of the antibodies, wherein a higher level of at least one of the antibodies compared to the control level of the antibodies indicates that the subject is likely to progress to CDMS within twenty-four months. In one aspect, a higher level of one of the antibodies in the test sample compared to the control level of the antibodies indicates the subject is at risk of having a second neurological attack within forty-eight months. Suitable test samples include whole blood, serum, or plasma. Preferably, the antibodies are IgM isotype antibodies.

The invention also provides methods of identifying a subject with a clinically isolated syndrome (CIS) suggestive of MS who will progress to clinically definitive multiple sclerosis (CDMS) within twenty-four months by providing a test sample from a subject and detecting in the test sample antibodies to a polymer comprising Glc ($\alpha$ 1,3) Glc ($\alpha$) and Glc ($\alpha$ 1,6) Glc ($\alpha$) disaccharides (P63). The levels of the antibodies in the test sample are compared to a control level of the antibodies, wherein a higher level of at least one of the antibodies compared to the control level of the antibodies indicates that the subject is likely to progress to CDMS within twenty-four months. In one aspect, a higher level of one of the antibodies in the test sample compared to the control level of the antibodies indicates the subject is at risk of having a second neurological attack within forty-eight months. Suitable test samples include whole blood, serum, or plasma. Preferably, the antibodies are IgM isotype antibodies.

The invention also provides methods for determining whether a patient has a higher risk for conversion to clinically defined multiple sclerosis (CDMS). First, a sera sample is obtained from a patient. Next, the level of antibodies to a polymer comprising Glc ($\alpha$ 1,3) Glc ($\alpha$) and/or Glc ($\alpha$ 1,6) Glc ($\alpha$) disaccharides in the sera sample is measured. Optionally, the antibody levels are detected via binding to glycans in a chamber or well, and increasing the optical density signal of the solution in the chamber. A classification rule is calculated based on the patient's age and the level of the antibodies in the sera sample. Finally, a risk factor based on the classification rule is outputted. In one aspect, the risk factor indicates that the patient has a higher risk for conversion to CDMS within 24 months. Optionally, the classification rule equals 1.17 minus (0.08*the age of the patient in years) plus (0.015*anti-P63(EU)). In one aspect, the risk factor is high if the classification rule is greater than or equal to 0.61. Optionally, sera sample is obtained after a first neurological event.

The invention also provides a computer-readable medium having computer-executable instructions for performing a method. First, a first variable associated with the level of at least one of an anti-Glc($\alpha$1,6)Glc($\alpha$) antibody, or an anti-Glc($\alpha$1,3)Glc($\alpha$) antibody, or an anti-P63 polymer antibody in a sera sample of a patient is stored. Next, a second variable associated with the age of the patient is stored. The patient's risk factor for conversion to clinically diagnosed multiple sclerosis is calculated as a function of at least the first and second variables. Finally, the risk factor is outputted. Optionally, the level of anti-P63 antibody in the sera sample is measured. In one aspect, the risk factor is high if the quantity (1.17−(0.08*the second variable)+(0.015*the first variable)) is greater than or equal to 0.61. Optionally, the risk factor is associated with the patient's conversion to clinically diagnosed multiple sclerosis within 24 months.

Also within the invention are reagents for diagnosing and predicting conversion of CIS patients to CDMS, wherein at least one of an anti-Glc($\alpha$1,3)Glc($\alpha$) antibody or an anti-Glc($\alpha$1,6)Glc($\alpha$) antibody are detected. In one aspect, the reagents are connected to a substrate via a linker. The substrate is a bead particles or a planer substrate. The glycan is a synthesized disaccharide or a natural polymer with repeating units of Glc($\alpha$1,3)Glc($\alpha$) and Glc($\alpha$1,6)Glc($\alpha$) either synthesized or extracted from an organism. For example, the anti-Glc($\alpha$1,6)Glc($\alpha$) or anti-Glc($\alpha$1,3)Glc($\alpha$) antibody is detected using the polysaccharide Dextran as an antigen.

In one embodiment, the glycan-containing molecule is provided on an oligosaccharide that comprises, e.g., 2-20, 2-18, 3-15, or 5-12 monosaccharides. In another aspect, at least one of the glycan-containing molecules are present on a polysaccharide. In yet another embodiment, the glycan-containing molecule is immobilized on a solid substrate.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
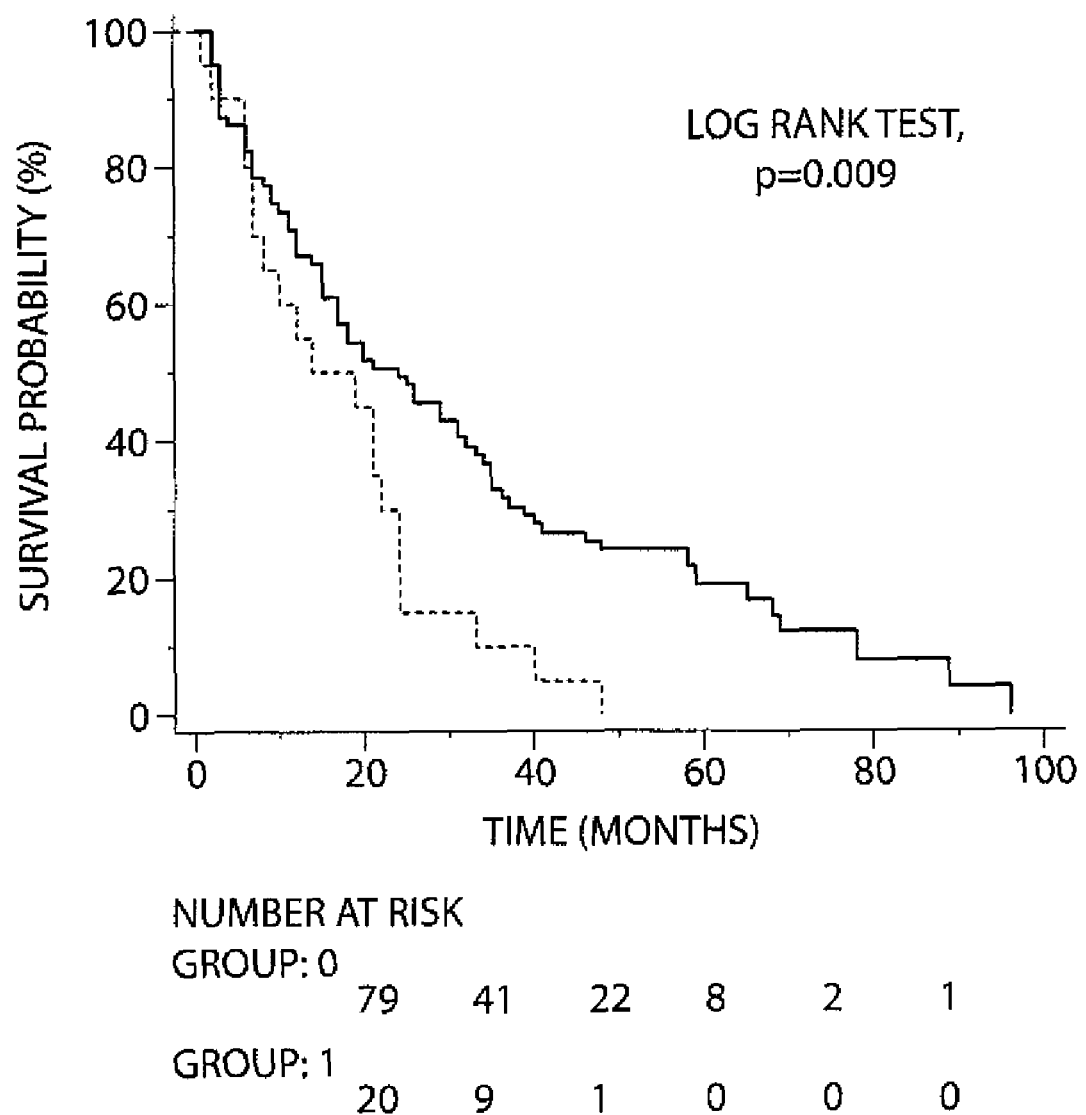
FIG. 1 shows a Kaplan-Meier survival plot for time to CDMS. CIS patients, n=99. Patients were classified as positive (above cutoff, dashed line) or negative (below cutoff, full line) by the following classifier based on a combination of anti-P63 and age: p=1.170703−0.082399·age (years)+ 0.015471·anti-P63 (EU). If p$\geq$0.6114674, the patient was classified as positive.

Multiple sclerosis (MS) is an inflammatory demyelinating disease of the central nervous system (CNS), though the exact etiology and pathogenesis have not yet been deciphered. Diagnosis of MS requires exclusion of diseases that could better explain the clinical, imaging and paraclinical findings. In order to diagnose a patient with MS, two separate events disseminate in time and space (different organs) must be recorded. The MS diagnosis criteria, also known as the revised McDonald criteria, define the parameters required for a subject having MS (Polman et al., 2005 Ann Neurol, 58: 840-6). To better define suspected MS cases that may or may not meet the McDonald criteria, an International Panel of MS experts recently developed consensus-determined guidelines for differential diagnosis leading to MS (Miller et al., 2008 Multiple Sclerosis, 14:1157-1174).

The course of MS disease follows unpredictable patterns of evolution and widely variable timetables, with disability accumulation adhering to no particular blueprint making it difficult or impossible to accurately determine the prognosis of individual patients (Vollmer T, 2007 J Neurol Sci, 256 Suppl 1:S5-13). Recently, clinically isolated syndrome (CIS) was "re-defined" as a monophasic presentation with suspected underlying inflammatory demyelinating disease (Miller D H et al., 2008 Multiple Sclerosis, 14:1157-1174). "Monophasic presentation" implies a single clinical episode at first presentation that is of relatively rapid onset. Multiple simultaneous clinical/paraclinical presentations (representing dissemination in space) are possible, although dissemination in time should not be evident. Four classes of CIS were defined based on whether the monophasic clinical presentation has mono- or multifocal clinical or MRI features (Miller D H et al., 2008 Multiple Sclerosis, 14:1157-1174). Finally, for CIS, there should be reasonable grounds for suspecting inflammatory demyelinating disease as the underlying pathology.

The search has been ongoing for useful serum derived biomarkers, including antibodies. Serum IgM antibodies to an N-glucosylated peptide were specifically increased in relapsing remitting multiple sclerosis (RRMS) patients (Lolli F, et al. 2005 Proc Natl Acad Sci USA, 102: 10273-78; Lolli F, et al. 2005 J Neuroimmunol, 167: 131-37). High antibody titers to two myelin peptides, myelin oligodendrocyte glycoprotein (MOG) and myelin basic protein (MBP), were reported by some (Berger T, et al. 2003 N Engl J Med, 349: 139-45), but not others (Kuhle J, et al. 2007 N Engl J Med, 356: 371-78) to predict early relapse in CIS patients. The finding of IgG antibody formation specifically in the cerebrospinal fluid (CSF), but not in a corresponding serum (i.e., oligoclonal banding), has been a useful test for diagnosis and differential diagnosis of MS (Freedman M S, et al. 2005 Arch Neurol, 62:865-70). Moreover, recent results show elevated levels of IgM antibodies to Glc ($\alpha$1,4) Glc ($\alpha$) (GAGA4) in RRMS patients in comparison to patients with other neurological diseases (OND) (Schwarz M, et al. 2006 J Neurol Sci, 244: 59-68). It was previously shown that patients with a first presentation of an acute neurological event suggestive of MS had a higher risk for conversion to RRMS within 2 years if they had high levels of anti-GAGA4 or anti-GlcNAC IgM (above median level of the cohort) (U.S. patent application Ser. No. 11/345,190).

Prior to the invention, there was no specific panel of serum-based biomarkers known for the diagnosis or prognosis of relapsing-remitting multiple sclerosis (RRMS). Additionally, prior to the invention, no known antigenic specificity profile existed to aid in the determination of disease activity (next relapse). The methods described herein that provide information regarding next relapse allow physicians to appropriately tailor therapeutic intervention. For example, a patient who is incorrectly considered to be unlikely to develop clinically definite MS (CDMS) within 24 months based on current methods (the lack of an abnormal MRI scan at FP (CIS type IV)) could begin aggressive treatment if the methods of the invention indicate that the patient is likely to progress to CDMS within 24 months. The information provided by the methods herein is also used to persuade CIS patients with an abnormal MRI scan to begin DMT, i.e., those patients at high risk for conversion to CDMS that would otherwise prefer to wait until their next relapse before beginning the inconvenient $1^{st}$ line DMT, which are given by injections.

The invention solves a long standing problem in the field of MS—how to determine a medical treatment regimen for a subject at clinically isolated syndrome (CIS). The method involves characterizing an individual as a member of one of two groups: (i) those who are likely to progress to clinically definite multiple sclerosis (CDMS) rapidly, i.e., within 24 months, and (ii) those who are likely to progress to CDMS relatively slowly, i.e., within greater than 24 months. Segregating patients at CIS based on the relative risk of progression is a critical factor in the determination of a treatment regimen, because those in group (i) receive an aggressive disease modifying therapy (DMT) regimen, whereas those in group (ii) receive a less aggressive DMT regimen. An aggressive regimen is characterized as a higher dose, more frequent dosing, or a more potent DMT compared to the less aggressive regimen.

During symptomatic attacks, administration of high doses of intravenous corticosteroids, such as methylprednisolone is the routine therapy for acute relapses. The aim of this kind of treatment is to end the attack sooner and leave fewer lasting deficits in the patient. Although generally effective in the short term for relieving symptoms, corticosteroid treatments do not appear to have a significant impact on long-term recovery (Brusaferri and Candelise, 2000 J. Neurol., 247 (6): 435-42). Potential side effects include osteoporosis and impaired memory, the latter being reversible (Dovio et al., 2004 Clin. Endocrinol. Metab., 89 (10): 4923-8; Uttner et al., 2005 Neurology, 64 (11): 1971-3). Severe attacks which do not respond to corticosteroids might be treated by plasmapheresis. The earliest clinical presentation of relapsing-remitting MS (RRMS) is the clinically isolated syndrome (CIS). Several studies have shown that treatment with interferons during an initial attack can decrease the chance that a patient will develop clinical MS (Jacobs et al., 2000 N Engl J Med, 343 (13): 898-904; Comi et al., 2001 Lancet, 357 (9268): 1576-82; Kappos et al., 2007 Lancet, 370 (9585): 389-97). These and other CIS studies that showed the benefits of early treatment with DMT lead to the current clinical practice in which newly diagnosed RRMS and CIS patients suggestive of MS are initiating DMT treatment immediately after first presentation and an abnormal MRI scan.

Six disease-modifying treatments have been approved by regulatory agencies of different countries for RRMS (Rudick and Polman 2009, Lancet Neurol, 8: 545-559). Three are interferons: two formulations of interferon beta-1a (trade names Avonex®, CinnoVex™, ReciGen and Rebif®) and one of interferon beta-1b (U.S. trade name Betaseron®, in Europe and Japan Betaferon®). A fourth medication is glatiramer acetate (Copaxone®). The fifth medication, mitoxantrone, is an immunosuppressant also used in cancer chemotherapy, approved only in the USA and largely for secondary progressive MS. The sixth is natalizumab (marketed as Tysabri). All six medications are modestly effective at decreasing the number of attacks and slowing progression to disability, although their efficacy rates differ, and studies of their long-term effects are still lacking (Ruggieri et al., 2007 CNS Drug Rev, 13 (2): 178-91; Munari et al., *Cochrane Database of Systematic Reviews* 2003, Issue 4. Art. No.: CD004678; Rice et al., 2001 *Cochrane Database Syst Rev* (4): CD002002; Martinelli Boneschi et al., 2005 *Cochrane Database Syst Rev* (4): CD002127). Comparisons between immunomodulators (all but mitoxantrone) show that the most effective is natalizumab, both in terms of relapse rate reduction and halting disability progression (Johnson K P, 2007 J. Neurol. Sci., 256 Suppl 1: S23-8); it has also been shown to reduce the severity of MS. Mitoxantrone may be the most effective of them all (Gonsette R E, 2007 Expert opinion on pharmacotherapy, 8 (8): 1103-16); however, it is generally not considered as a long-term therapy, as its use is limited by severe cardiotoxicity (Murray T J, 2006 Expert opinion on drug safety, 5 (2): 265-74). The interferons and glatiramer acetate are delivered by frequent injections, varying from once-per-day for glatiramer acetate to once-per-week (but intra-muscular) for Avonex®. Natalizumab and mitoxantrone are given by IV infusion at monthly intervals.

Treatment of progressive MS is more difficult than relapsing-remitting MS. Mitoxantrone has shown positive effects in patients with secondary progressive and progressive relapsing courses. It is moderately effective in reducing the progression of the disease and the frequency of relapses in patients in short-term follow-up (Martinelli Boneschi F et al., 2005 *Cochrane Database Syst Rev* (4): CD002127). No treatment has been proven to modify the course of primary progressive MS (Leary and Thompson, 2005 CNS drugs, 19 (5): 369-76).

The methods are typically performed using reagents that specifically bind to the anti-glycan antibodies. The reagents can be, e.g., the specific glycan structures. Alternatively, the reagents can be other molecules or macromolecules that include the specific glycan structure. In some embodiments, the reagents that are used to specifically bind and detect those anti glycan antibodies are the specific glycan structures. In other embodiments, the reagents are other molecules that include the specific glycan structure. The glycan or sugar structures can be only the carbohydrate moiety (including a monosaccharide, an oligosaccharide, or a polysaccharide) or displaying on any solid phase or other macromoleculeor any other molecular structure that includes the glycan. The glycan-containing structure can be naturally occurring, e.g., extracted from an organism, or synthetic. For example, the Glc($\alpha$1,3)Glc($\alpha$) antibody can be detected using a polysaccharide that includes a polymer with one or more Glc($\alpha$1,3)Glc($\alpha$) linkages.

In another example, the anti-Glc($\alpha$1,6)Glc($\alpha$) or anti-Glc($\alpha$1,3)Glc($\alpha$) antibody is detected using the polysaccharide dextran as an antigen. Dextran is a polymer of sugar units connected with one or more Glc($\alpha$1,6)Glc($\alpha$) glycosidic bonds with some Glc($\alpha$1,3)Glc($\alpha$) branches. Thus, the glycan itself can be used for detecting the corresponding antibody or antibodies, as can any other molecular structure that includes the glycan.

If desired, peptides that mimic carbohydrate antigens can be used in the methods and compositions described herein. The peptides can be used to identify specific anti glycan antibodies. Peptides which mimic structures recognized by anti-glycan antibodies can be identified using methods known in the art, e.g., by screening a filamentous phage-displayed random peptide library (Zhan et al., 2003 Biochem Biophys Res Commun, 308:19-22; Hou et al., 2003 J Immunol, 17: 4373-79).

Glycan antigens used to identify various anti-glycan antibodies can be obtained from a variety of other sources so long as the antigen is capable of binding specifically to the given anti-glycan. Binding to anti-glycan antibodies can be performed using a variety of other immunoassay formats known in the art, including competitive and non-competitive immunoassay formats can also be used (Self and Cook, Curr. Opin. Biotechnol., 7:60-65 (1996), which is incorporated by reference). Other assays include immunoassays, such as enzyme-linked immunosorbent assays (ELISAs). An enzyme such as horseradish peroxidase (HRP), alkaline phosphatase (AP), $\beta$-galactosidase or urease can be linked to a secondary antibody selective for a primary anti-glycan antibody of interest. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a $\beta$-galactosidase detection system can be used with the chromogenic substrate o-nitrophenyl-a $\beta$-D-galactopyranoside (ONPG), which yields a soluble product detectable at 410 nm, or a urease detection system can be used with a substrate such as urea-bromocresol purple (Sigma Immunochemicals, St. Louis, Mo.). A useful secondary antibody linked to an enzyme can be obtained from a number of commercial sources; goat F(ab')$_2$ anti-human IgG-alkaline phosphatase, for example, can be purchased from Jackson Immuno-Research (West Grove, Pa.).

Immunoassays encompass capillary electrophoresis based immunoassays (CEIA) and can be automated, if desired. Immunoassays also can be used in conjunction with laser induced fluorescence (see, for example, Schmalzing and Nashabeh, Electrophoresis 18:2184-93 (1997)); Bao, J. Chromatogr. B. Biomed. Sci. 699:463-80 (1997), each of which is incorporated herein by reference). Liposome immunoassays, such as flow-injection liposome immunoassays and liposome immunosensors, also can be used (Rongen et al., J. Immunol., Methods 204:105-133 (1997)).

A radioimmunoassay can also be used for determining whether a sample is positive for a glycan antibody, or for determining the level of anti-glycan antibodies in a sample. A radioimmunoassay using, for example, an $^{125}$Iodine-labeled secondary antibody (Harlow and Lane, Antibodies A Laboratory Manual Cold Spring Harbor Laboratory: New York, 1988, which is incorporated herein by reference) is encompassed within the invention.

A secondary antibody may alternatively be labeled with a chemiluminescent marker. Such a chemiluminescent secondary antibody is convenient for sensitive, non-radioactive detection of anti-glycan antibodies and can be obtained commercially from various sources such as Amersham Lifesciences, Inc. (Arlington Heights, Ill.).

A detectable reagent may also be labeled with a fluorochrome. Appropriate fluorochromes include, for example, DAPI, fluorescein, Hoechst 33258, R-phycocyanin, B-phycoerythrin, R-phycoerythrin, rhodamine, Texas red or lissamine. A particularly useful fluorochrome is fluorescein or rhodamine. Secondary antibodies linked to fluorochromes can be obtained commercially. For example, goat $F(ab')_2$ anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of $^{125}$Iodine; or a fluorometer to detect fluorescence in the presence of light of a certain wavelength. For detection of enzyme-linked reagents, a quantitative analysis of the amount of anti-glycan antibodies can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Other methods include, e.g., flow cytometry (including bead based immunoassays), and phage display technology for expressing a recombinant antigen specific for an anti-glycan antibody. Phage particles expressing the antigen specific for a desired anti-glycan antibody can be anchored, if desired, to a multiwell plate using an antibody such as an anti phage monoclonal antibody (Felici et al., "Phage-Displayed Peptides as Tools for Characterization of Human Sera" in Abelson (Ed.), Methods in Enzymol. 267, San Diego: Academic Press, Inc. (1996), which is incorporated by reference herein).

Interpreting Anti-Glycan Antibody Binding Data

Typically, binding of anti-glycan antibodies to glycans in a sample is compared to a reference sample or samples, and differences in levels of the anti-glycan antibodies in the two samples are compared. The threshold for determining whether a test sample is scored positive based on its anti-glycan antibodies levels can be altered depending on the sensitivity or specificity desired. The clinical parameters of sensitivity, specificity, negative predictive value, positive predictive value and efficiency are calculated using true positives, false positives, false negatives and true negatives. A "true positive" sample is a sample that is positive according to an art recognized method (a sample from a CIS patient known to experience a second neurological attack during the twenty-four months after the first neurological attack), which is also diagnosed as positive (high risk for early attack) according to a method of the invention. A "false positive" sample is a sample negative by an art-recognized method (a sample from CIS patient who did not experience a second neurological attack during the twenty-four months), which is diagnosed positive (high risk for early attack) according to a method of the invention. Similarly, a "false negative" is a sample positive for an art-recognized analysis, which is diagnosed negative according to a method of the invention. A "true negative" is a sample negative for the assessed trait by an art-recognized method, and also negative according to a method of the invention. See, for example, Mousy (Ed.), Intuitive Biostatistics New York: Oxford University Press (1995), which is incorporated herein by reference.

As used herein, the term "sensitivity" means the probability that a laboratory method is positive in the presence of the measured trait. Sensitivity is calculated as the number of true positive results divided by the sum of the true positives and false negatives. Sensitivity essentially is a measure of how well a method correctly identifies those with disease. In a method of the invention, the anti-glycan antibody cut-off values can be selected such that the sensitivity of diagnosing an individual is at least about 60%, and can be, for example, at least about 65%, 70%, 75%, 80%, 85%, 90% or 95%.

As used herein, the term "specificity" means the probability that a method is negative in the absence of the measured trait. Specificity is calculated as the number of true negative results divided by the sum of the true negatives and false positives. Specificity essentially is a measure of how well a method excludes those who do not have the measured trait. The anti-glycan cut-off value can be selected such that, when the sensitivity is at least about 70%, the specificity of diagnosing an individual is in the range of 30-60%, for example, 35-60%, 40-60%, 45-60% or 50-60%.

The term "positive predictive value," as used herein, is synonymous with "PPV" and means the probability that an individual diagnosed as having the measured trait actually has the disease. Positive predictive value can be calculated as the number of true positives divided by the sum of the true positives and false positives. Positive predictive value is determined by the characteristics of the diagnostic method as well as the prevalence of the disease in the population analyzed. In a method of the invention, the anti-glycan antibody cut-off values can be selected such that the positive predictive value of the method in a population having a disease prevalence of 15% is at least about 5%, and can be, for example, at least about 8%, 10%, 15%, 20%, 25%, 30% or 40%.

As used herein, the term "efficiency" means the accuracy with which a method diagnoses a disease state. Efficiency is calculated as the sum of the true positives and true negatives divided by the total number of sample results and is affected by the prevalence of the trait in the population analyzed. The anti-glycan antibody cut-off values can be selected such that the efficiency of a method of the invention in a patient population having an MS disease prevalence of 15% is at least about 45%, and can be, for example, at least about 50%, 55% or 60%.

The classification rule for identifying patients at high risk based on the methods of this invention was developed as follows. One aspect of this method is related to using the levels of the anti-Glc($\alpha$1,6)Glc($\alpha$) and anti-Glc($\alpha$1,3)Glc($\alpha$) antibodies, or levels of antibodies to a polymer comprising Glc($\alpha$1,6)Glc($\alpha$) and Glc($\alpha$1,3)Glc($\alpha$), together with other variants known to affect the risk (e.g., age of the patient, MRI results, and genetic factors) for classification of the patient's risk for having a second neurological attack during the twenty-four months after the first neurological attack. The anti-glycan antibodies of this invention are polyclonal, and the measurement of the levels in the tested sample is performed by semi-quantitative methods, e.g., the levels are reflected in relative units, and not by absolute units (e.g., micrograms of antibody/Litter). Therefore, for each measurement method, different coefficients and classifier cut-off values are calculated. There are several statistical methods for the development of the coefficients and parameters and cut-off for the classifier. Logistic regression can be used for classifier development in the following way:

A cohort of CIS patients are followed for up to 24 months or 48 months from the CIS event. The information regarding having or not having a second relapse within the follow-up time is recorded. A database is prepared with the levels of antibodies, along with demographic and clinical baseline characteristics, and whether or not the patient had a second relapse within the follow up time. Logistic regression models are used to identify the parameters that are significantly associated with the risk for an early second attack and to construct a classifier equation for calculation of the classifier levels based on the relevant parameters (e.g., anti-P63 levels and age).

For determination of the cut-off level, receiver operating characteristic (ROC) curve analysis can be used. A plot is prepared for sensitivity versus 1-specificity for all possible cut-off values for differentiation between patients who convert to CDMS (had a second attack) within 24 months versus patients who did not convert to CDMS.

The cut-off value for the classifier can be determined as the value that provides specificity of at least 90%, at least 80% or at least 70% and a maximum sensitivity. An alternative way for identifying an optimal cut-off level for differentiation between patients who convert to CDMS, versus patients who did not convert to CDMS can be performed by calculation of the Youden index. This index is defined as $J=\max_c\{Se(c)+Sp(c)-1\}$ and ranges between 0 and 1 (Youden W J, 1950 Cancer, 3: 32-35). At the point of maximal Youden index, maximal Sensitivity and Specificity, are achieved.

The invention will be illustrated in the following non-limiting examples.

Example 1

P63 and Age for Prediction of Early CDMS Conversion

Described below is a method for the identification of clinically isolated syndrome (CIS) patients suggestive of multiple sclerosis having a higher risk for conversion to CDMS within 24 months. A classification rule was developed based on anti-Glc($\alpha$1,6)Glc($\alpha$) and anti-Glc($\alpha$1,3)Glc($\alpha$) polymer (such as dextran (P63)) IgM antibody level in the sera of a patient, along with patient age. This classification rule predicts a higher risk for conversion to clinically defined MS (CDMS) within 24 months. The classification rule was analyzed in a different cohort including 99 CIS patients from Canada and Belgium.

A retrospective prospective analysis was performed on 99 frozen sera samples taken from CIS patients during MS diagnosis workup. The patients were followed for at least 48 months and the time to conversion to CDMS criteria was recorded. Levels of anti-P63 IgM antibodies in the sera samples were measured by enzyme immunoassay (EIA). A classification rule based on levels of anti-P63 IgM in patient serum, along with patient age was used to identify risk for early relapse within $\leq$24 months. Kaplan-Meier survival analysis estimate was used to estimate the cumulative number of CIS survival between CIS patients that were positive versus CIS patients negative based on the classifier.

At 24 months, the Kaplan-Meier survival analysis estimate, i.e., the estimated percentage of patients converted to CDMS, of the group that was classified as negative was 50% CIS patients who did not convert to CDMS compared to 15% in the group classified as positive. Median survival time for the positive patients was 14 months, versus 24 months for the negative (P=0.009, log rank test), and the hazard ratio was 1.9 (95CI 1.2-4.4) for early conversion to CDMS. As described in detail below, a classification rule based on levels of anti-P63 IgM in patient serum, along with patient age was analyzed.

At 48 months, the Kaplan-Meier survival analysis estimate, i.e., the estimated percentage of patients converted to CDMS, of the group that was classified as negative was 25.8% CIS patients who did not convert to CDMS compared to 0.0% in the group classified as positive. Median survival time for the positive patients was 14 months, versus 24 months for the negative (P=0.009, log rank test), and the hazard ratio was 1.9 (95CI 1.2-4.4) for early conversion to CDMS. As described in detail below, a classification rule based on levels of anti-P63 IgM in patient serum, along with patient age was analyzed.

Materials and Methods

A retrospective study was performed on frozen (−70° C.) and re-thawed serum samples collected from patients at the time of diagnostic work-up for their first presentation (FP) who were later diagnosed as RRMS (Freedman M S et al., 2009 *Mult Scler*, 15(4):422-30). Demographic and clinical data were obtained from hospital records. Inclusion criteria for MS samples were: patient age (18-60 years) at time of sampling, follow-up for at least 4 years from blood sampling, and diagnosis of RRMS according to Poser criteria (Poser C M, et al., 1983 *Ann Neurol*, 13:227-231). Samples meeting the above criteria were identified from one of two serum repositories located at the Ottawa Hospital-General Campus, Ottawa, Canada between the years 1993 to 2001 or the Cliniques Universitaires Saint-Luc in Brussels, Belgium between the years 1998 to 2002. Samples were collected under a broad consent for scientific research allowing for multiple studies and approved by local ethics boards. Relapse was defined as any new neurological event accompanied by symptoms or signs, or significant worsening of previous symptoms or signs in the absence of fever that lasted at least 48 hours. The cohort included 99 FP patients.

EIA Procedures

The serum samples were stored frozen and were transported frozen to Glycominds Ltd., Lod, Israel. Samples were stored in −20° C. until use. Prior to use, samples were thawed by incubation in 37° C. for 2 hours. IgG depletion was performed using a commercial mini Rapi-Sep® units (PanBio, Baltimore, Md., USA). Serum samples were diluted 1:600 in a sample diluent, dispensed into the wells in duplicates, and incubated for 180 min in 4° C., then washed with wash buffer. Bound antibodies were labeled with horseradish peroxidase (HRP)-conjugated goat anti-human IgM type-specific antibody, washed, and 3,3'5,5'-tetramethylbenzidine was added for detection. After 30 minutes, the enzymatic reaction was stopped with 1% sulfuric acid solution and optical density (OD) in the wells was read at 450 nm with a microwell plate reader (Wallac, Turku, Finland). Each plate included a 5 point calibration curve with a preset unit value for each point on the curve. Measurements were done in duplicates, each plate included a 5 point calibration curve to normalize results obtained from different plates. Results were reported in arbitrary EIA Units (EU).

Statistical Analysis

Patients were classified as positive or negative based on levels of sera anti-P63 IgM and patient age using the classifier described above: p=1.170703−0.082399·age (years)+ 0.015471·anti-P63 (EU). If p≧0.6114674, the patient was classified as positive with a risk for early relapse within ≦24 months.

The cumulative risk of the development of clinically definite MS (CDMS) was calculated for each group according to the Kaplan-Meier method, and differences between the groups were evaluated in a univariate analysis by the log-rank test. P-values of less than 0.05 were considered to be statistically significant. The median survival time and hazard ratio for positive versus negative patients was calculated. Uncertainty of results was expressed by 95% confidence intervals.

Results

Out of the 99 CIS patients, 20 were positive for the classifier and 79 were negative. The median survival time for the positive patients was 14 months, versus 24 months for the negative (P=0.009, log rank test). The hazard ratio was 1.9 (95CI 1.2-4.4) for early conversion to CDMS. See, FIG. 1 and Table 1. These results show that the classifier identified was validated in an independent cohort.

Figure 2:
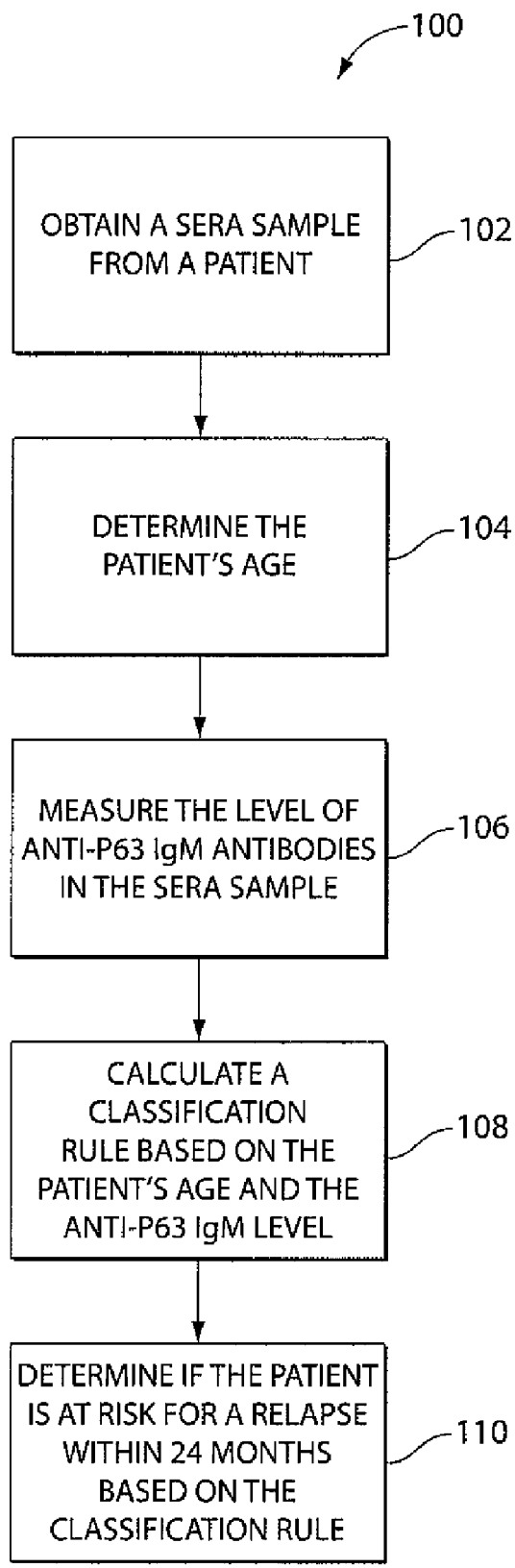
FIG. 2 is a block flow diagram of a process of determining whether a CIS patient is at risk of a relapse within 24 months.

FIG. 2 shows a process (100) for determining if a CIS patient is at risk for a conversion to CDMS within 24 months. In the process (100), a classification rule based on anti-P63 IgM antibodies in the sera of a patient in combination with the patient's age is calculated. The process (100), however, is exemplary only and not limiting. The process (100) may be altered, e.g., by having stages added, removed, or rearranged. The process (100) is implemented on a system including one or more computers or computer networks configured to read and execute computer-readable instructions stored on computer-readable mediums. A computer-readable medium can be defined as any kind of computer memory such as floppy disks, conventional hard disks, CD and DVD ROMS, Flash ROMS, nonvolatile ROM, and RAM.

At stage 102, a test sample, e.g., a sera sample, is obtained from a patient. Optionally, the patient's blood sample is collected by venipuncture. Following blood collection, the blood will clot, and the serum is separated from the blood clot by centrifugation of the collection tube. Sera samples are collected from a patient and stored prior to use, e.g., the sample is stored at −20° C., −70° C. or −80° C. until use. The patient's date of birth (i.e., age) is also determined (104). At stage 106, the level of an anti-Glc($\alpha$1,6)Glc($\alpha$) and anti-Glc($\alpha$1,3)Glc ($\alpha$) polymer (such as dextran (P63)) IgM antibodies in the sera of the patient is determined. Optionally, an IgG depletion can be performed using a commercial mini Rapi-Sep® units (PanBio, Baltimore, Md., USA). In one aspect, serum samples are diluted 1:600 in a sample diluent, dispensed into wells in duplicates, and incubated for 180 min in 4° C., then washed with wash buffer. Bound antibodies are labeled with horseradish peroxidase (HRP)-conjugated goat anti-human IgM type-specific antibody, washed, and 3,3',5,5'-tetramethylbenzidine is added for detection. After approximately 30 minutes, the enzymatic reaction is stopped with 1% sulfuric acid solution and the optical density (OD) in the wells is read at 450 nm with a microwell plate reader (Wallac, Turku, Finland).

The levels of the antibody in the test sample are not reported as a direct signal measured (e.g., fluorescence signal, optical density signal, or luminescence), but rather reported relative to a calibration sample with a predefined unit value (e.g., 50 units) that is included in each assay. The unit value of a test sample is calculated relative to the calibration sample as follows: test sample units=signal measured for test sample/ signal measured for calibration sample*units of calibration sample. For example, if Enzyme linked Immune Assay (EIA) technology is used for antibodies levels and the measured signal is Optical Density (OD) in the wells, then the EIA units (EU) will be calculated as: test sample EU=OD test sample/ OD calibration sample*units value of calibration sample.

At stage 108, a classification rule p is calculated. For example, as described above, the classification rule, p, can equal 1.170703 minus (0.082399*age) plus (0.015471*anti-P63 (EU)), where "age" is the age in years of the patient at the time the sera sample was collected, EU is the anti-P63 units value of the test sera sample that is calculated as described above.

At stage 110, the patient's risk of relapse (i.e., conversion to CDMS) is determined. For example, if the classification rule, p, calculated in stage 108 is greater or equal to 0.6114674, then the patient is classified as positive for a higher risk of relapse within 24 months. If the classification rule, p, calculated in stage 108 is less than 0.6114674, then the patient is classified as negative and will have a lower risk of relapse within 24 months.

Example 2

Anti-Glc($\alpha$1,6)Glc($\alpha$) and anti-Glc($\alpha$1,3)Glc($\alpha$) Polymer Antibody (P63) and Age Predict Early Conversion to CDMS A classification rule based on age, along with the level of anti-Glc($\alpha$1,6)Glc($\alpha$) and anti-Glc($\alpha$1,3)Glc($\alpha$) polymer (such as dextran (P63)) IgM antibody in the serum of a patient predicts a higher risk for early conversion to clinically definite MS (CDMS) in clinically isolated syndrome (CIS) patients suggestive of multiple sclerosis.

Described below is a method for identifying clinically isolated syndrome (CIS) patients suggestive of multiple sclerosis (MS) that have a higher risk for early conversion to CDMS within 24 months. A classification rule based on the level of anti-Glc($\alpha$1,6)Glc($\alpha$) and anti-Glc($\alpha$1,3)Glc($\alpha$) polymer (dextran (P63)) IgM antibodies in the serum of a patient, in combination with the patient's age indicate that a CIS patient has a higher risk for early conversion to clinically definite MS (CDMS) within 24 months.

As described in detail below, a prospective analysis was performed on 286 frozen sera samples taken from CIS patients that participated in the BENEFIT study at baseline (both placebo and treated groups). During the first 24 months, some patients were randomized to the Placebo group, while other patients were allocated to the treatment group. Each CIS patient under the Placebo group was transformed to the treatment group by the earlier of conversion to CDMS, or after 24 months. An additional 36 months of follow-up was analyzed for both "early" treatment and "delayed" treatment. During the 60 month follow-up period, the time to conversion to CDMS or conversion to MS based on the McDonalds criteria was recorded. Levels of anti-Glc($\alpha$1,6)Glc($\alpha$) and anti-Glc ($\alpha$1,3)Glc($\alpha$) polymer (dextran (P63)) IgM antibodies in the sera samples were measured by enzyme immunoassay (EIA). Based on the placebo group data (n=109, up to 24 months follow up), a logistic regression model including anti-P63 levels, clinical (conversion to CDMS within 24 months), and demographic data were used to develop a classifier for predicting risk for CDMS conversion within 24 months. Subsequently, further evaluation on the full cohort was performed (n=286, 60 month follow up).

Only age and anti-P63 IgM were included in the logistics regression model (classification rule). The classification rule enabled the identification of CIS patients at risk for early conversion to CDMS with 32.6% sensitivity, 75% positive predictive value (PPV), and 61.2% negative predictive value (NPV). At 60 months (day 1800), Kaplan-Meier survival analysis estimate, i.e., the estimated percentage of patients that did not convert to CDMS, of the group that was classified as Negative was 53.6%, compared to only 35.02% in the group classified as Positive (P=0.002, log rank test). The estimated percentage of patients who did not convert to McDonald MS (of the group that was classified as Negative) was 17.7%, in comparison to only 8.9% in the group classified as Positive (P=0.048, log rank test).

As described in further detail below, a classification rule based on levels of sera anti-P63 IgM antibodies and patient age was developed as follows: p=1.170703−0.082399·age (years)+0.015471·anti-P63(EU). If p≧0.6114674, then the patient was classified as positive with a risk for next relapse within ≦24 months. Kaplan-Meier survival analysis indicates that patients classified as positive (above cutoff) by the classifier have a higher risk for conversion to CDMS or McDonald MS both within 24 months as compared to patients who are negative (below cutoff).

BENEFIT Study and Retained Samples

The BENEFIT study (Betaferon®/Betaseron® in Newly Emerging MS for Initial Treatment) consisted of a placebo-controlled phase and a follow-up phase (Kappos L et al., 2007 *Lancet*, 4; 370 (9585): 389-97). The 2-year double-blinded, placebo-controlled phase, assessed the safety, tolerability, and efficacy of interferon beta-1b 250 μg (8 MIU) subcutaneously every other day in CIS patients with a first event suggestive of MS. Eligible patients had experienced a first neurological event suggestive of MS and had at least two clinically silent lesions on a T2-weighted brain magnetic resonance imaging (MRI) scan. Within 60 days of the onset of the first clinical event, and after providing written informed consent, patients were randomly assigned, in a 5:3 ratio, to interferon beta-1b 250 μg or placebo subcutaneously every other day. Patients completed the placebo-controlled phase by the earlier of when CDMS was diagnosed with the use of the modified Poser criteria (Poser C M, et al., 1983 *Ann Neurol*, 13: 227-231), or after 2 years. Patients who completed the placebo-controlled phase were eligible to enter the follow-up phase and, were offered interferon beta-1b 250 μg subcutaneously every other day for up to 5 years from randomization. This follow-up study continues to examine the delay of MS according to the new criteria (McDonald W I et al., 2001 *Ann Neurol*, 50: 121-27; Polman C P et al., 2005 *Ann Neurol*, 58: 840-6), as well as delay of CDMS by early treatment with IFNB-1b.

At baseline, sera from CIS patients with a first clinical event and at least two clinically silent lesions on T2-weighted brain MRI were taken. Regular follow-up visits were scheduled for the assessment of patient neurology impairment and for MRI before treatment and during the study. As described below, the placebo group as analyzed during the first 24 months was used for the development and evaluation of a classification rule that enables the prediction of conversion to CDMS within 24 months.

Enzyme Immunoassay for Anti-Glc(α1,6)Glc(α) and Anti-Glc(α1,3)Glc(α) Polymer Antibody (Dextran (P63)) IgM Levels Each sample was tested for levels of anti-P63 IgM using the EIA method in a 96 microwell plate. 96 microwell plates with the P63 antigen adsorbed to the walls of each microwell (Nunc, Sweden) were prepared by cyanuric chloride activation of the wells as previously described and dispensing to each well 50 μL of dextran solution. Following incubation for 16 hours, the wells were washed with distilled water, and subsequently washed with methanol and kept dry until use.

The serum samples were stored frozen and were transported frozen to Glycominds Ltd., Lod, Israel. Samples were stored in −80° C. until use. Prior to use, samples were thawed by incubation in 37° C. for 2 hours. IgG depletion was performed using a commercial mini Rapi-Sep® units (PanBio, Baltimore, Md., USA). Serum samples were diluted 1:600 in a sample diluent, dispensed into the wells in duplicates, and incubated for 180 min in 4° C., then washed with wash buffer. Bound antibodies were labeled with horseradish peroxidase (HRP)-conjugated goat anti-human IgM type-specific antibody, washed, and 3,3',5,5'-tetramethylbenzidine was added for detection. After 30 minutes, the enzymatic reaction was stopped with 1% sulfuric acid solution and optical density (OD) in the wells was read at 450 nm with a microwell plate reader (Wallac, Turku, Finland). Each plate included a 5 point calibration curve with a preset unit value for each point on the curve. Measurements were done in duplicates, each plate included a 5 point calibration curve to normalize results obtained from the different plates. Results were reported in arbitrary EIA Units (EU).

Statistical Analysis

The classifier development was based on logistic regression. A two step method was used. First, the model included only clinical baseline characteristics: (age in years, gender, and steroid treatment (yes/no)) in order to predict early conversion to CDMS. Later, anti-P63 data was added to the model for determination of the final classification rule. The two groups to be predicted were early CDMS (≦24 months) versus late CDMS (>24 months). The data used was the data from the placebo patients in the BENEFIT study only. Logistic regression with backward selection was used as the classifier model. A ten-fold cross-validation procedure was performed to avoid any bias in the estimation of predictive strength. This cross-validation procedure was repeated ten times with randomly sampled block constellation to avoid dependency on the partitioning. In a second step, all clinical variables remaining in the above classifier and anti-P63 IgM were used to construct a classifier for "early CDMS" versus "late CDMS".

The choice of a cut-off value for each classifier was based on the requirement of a specificity of at least 90%, i.e., the cut-off values were chosen such that a maximum sensitivity was reached with a specificity of at least 90%. Diagnostic accuracy was calculated by sensitivity, specificity, positive predictive value (PPV) and negative predictive value (NPV).

Numerical variables were compared across groups by Student's t-test or by the Mann-Whitney U-test, depending on whether or not they followed a normal distribution, and the $\chi^2$ test for rates comparison between groups. P-values of less than 0.05 were considered to be statistically significant. Uncertainty of results was expressed by 95% confidence intervals.

The cumulative risk of early conversion to CDMS or to MS based on the McDonald revised criteria was calculated for the group of positive (above cutoff) according to classifier 2 and to the group of negative (below cutoff) according to classifier 2, according to the Kaplan-Meier method, and differences between the groups were evaluated in a univariate analysis by the log-rank test.

Figure 3:
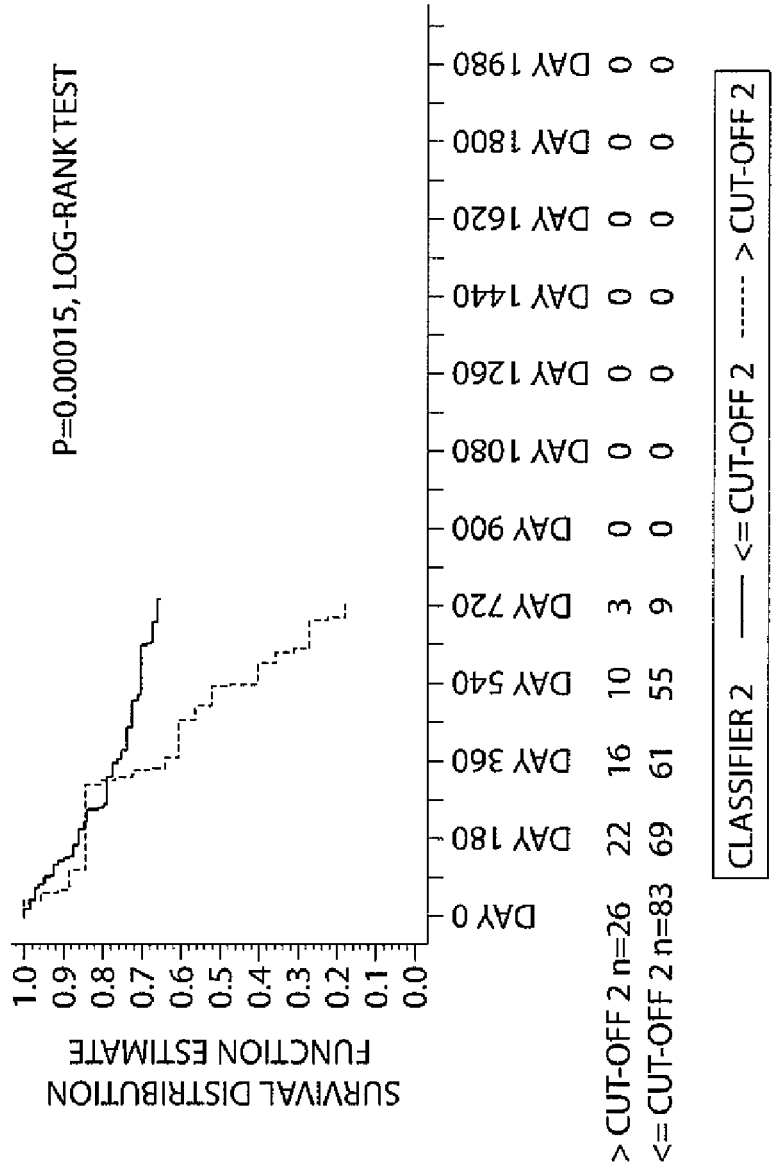
FIG. 3 shows a Kaplan-Meier survival plot for time to CDMS. CIS patient placebo arm, n=109. Patients were classified as positive (above cutoff, dashed line) or negative (below cutoff, full line) by a classifier based on combination of anti-P63 and age: p=1.170703−0.082399·age (years)+ 0.015471·anti-P63 (EU). If p≧0.6114674, the patient was classified as positive.

The placebo group included 109 CIS patients. The variable of age at diagnosis was included in the model. After inclusion of anti-P63 IgM levels in the second step, both variables remained in the model for prediction of risk for early CDMS conversion. The final classification rule and it's diagnostic performance at 90% specificity are described in Table 2. In the placebo cohort, the classification rule enabled the identification of CIS patients at risk for early conversion to CDMS with 32.6% sensitivity, 75% PPV, and 61.2% NPV. The results of the Kaplan-Meier estimate analysis for day 720 for the placebo cohort is described in FIG. 3 and Table 3, while Table 5 describes the detailed data.

TABLE 1

Raw data for FIG. 1

| Sample ID | Gender M = Male, F = Female | Age (Years) | anti-P63 IgM units (EU) | Had a relapse event with in follow up time (Yes/No) | Time to next relapse, or time to end of followup (months) | Classifier level | Classifier status: 1 if ≧0.6114674, 0 if <0.6114674 |
|---|---|---|---|---|---|---|---|
| 12394 | M | 58 | 40.1 | yes | 15 | −2.99 | 0 |
| 13602 | F | 56 | 38.9 | yes | 20 | −2.84 | 0 |
| 13527 | M | 56 | 45.4 | yes | 2 | −2.74 | 0 |
| 13585 | M | 57 | 74.4 | yes | 6 | −2.37 | 0 |
| 13546 | F | 54 | 68.9 | yes | 7 | −2.21 | 0 |
| 12404 | F | 52 | 53.0 | yes | 6 | −2.29 | 0 |
| 13536 | F | 53 | 69.9 | No | 48 | −2.11 | 0 |
| 13547 | F | 59 | 129.8 | No | 48 | −1.68 | 0 |
| 13646 | F | 55 | 100.1 | yes | 12 | −1.81 | 0 |
| 13587 | M | 49 | 52.4 | No | 48 | −2.06 | 0 |
| 13604 | M | 48 | 73.3 | yes | 7 | −1.65 | 0 |
| 12373 | F | 49 | 83.0 | yes | 65 | −1.58 | 0 |
| 13514 | M | 44 | 62.1 | yes | 2 | −1.49 | 0 |
| 13606 | M | 45 | 85.6 | No | 48 | −1.21 | 0 |
| 13626 | M | 43 | 73.4 | yes | 3 | −1.24 | 0 |
| 13580 | F | 41 | 61.2 | yes | 3 | −1.26 | 0 |
| 13623 | F | 42 | 69.3 | No | 48 | −1.22 | 0 |
| 13581 | F | 49 | 130.0 | yes | 18 | −0.86 | 0 |
| 12466 | F | 41 | 66.2 | yes | 20 | −1.18 | 0 |
| 13639 | M | 40 | 60.1 | No | 48 | −1.20 | 0 |
| 13642 | F | 45 | 100.4 | No | 48 | −0.98 | 0 |
| 12360 | M | 41 | 72.2 | yes | 78 | −1.09 | 0 |
| 12403 | M | 41 | 72.3 | yes | 58 | −1.09 | 0 |
| 13557 | M | 41 | 75.3 | yes | 34 | −1.04 | 0 |
| 12459 | M | 42 | 89.2 | yes | 15 | −0.91 | 0 |
| 12389 | M | 40 | 81.4 | yes | 3 | −0.87 | 0 |
| 13591 | M | 37 | 59.4 | No | 48 | −0.96 | 0 |
| 13597 | M | 38 | 67.6 | No | 48 | −0.91 | 0 |
| 13502 | F | 43 | 110.0 | No | 72 | −0.67 | 0 |
| 13515 | F | 46 | 135.9 | yes | 41 | −0.52 | 0 |
| 13543 | M | 42 | 112.8 | yes | 2 | −0.55 | 0 |
| 13603 | F | 41 | 105.2 | yes | 15 | −0.58 | 0 |
| 12336 | F | 40 | 97.5 | yes | 9 | −0.62 | 0 |
| 12339 | F | 42 | 115.4 | yes | 35 | −0.50 | 0 |
| 12433 | F | 42 | 115.9 | yes | 26 | −0.50 | 0 |
| 13607 | F | 36 | 67.9 | yes | 8 | −0.75 | 0 |
| 12385 | M | 36 | 71.3 | yes | 31 | −0.69 | 0 |
| 12412 | F | 40 | 108.3 | yes | 33 | −0.45 | 0 |
| 13566 | M | 39 | 102.5 | yes | 18 | −0.46 | 0 |
| 12425 | M | 40 | 110.9 | yes | 35 | −0.41 | 0 |
| 12397 | F | 34 | 68.0 | yes | 69 | −0.58 | 0 |
| 12158 | F | 32 | 53.5 | yes | 29 | −0.64 | 0 |
| 12328 | F | 37 | 97.4 | yes | 17 | −0.37 | 0 |
| 13572 | M | 40 | 123.4 | yes | 3 | −0.22 | 0 |
| 12398 | F | 33 | 69.4 | yes | 48 | −0.48 | 0 |
| 12320 | F | 34 | 80.3 | yes | 96 | −0.39 | 0 |
| 12391 | M | 36 | 99.1 | yes | 68 | −0.26 | 0 |
| 12372 | F | 32 | 70.1 | yes | 17 | −0.38 | 0 |
| 13592 | M | 32 | 71.8 | yes | 36 | −0.36 | 0 |
| 12422 | F | 31 | 68.5 | yes | 6 | −0.32 | 0 |
| 13637 | M | 34 | 97.0 | yes | 11 | −0.13 | 0 |
| 12437 | F | 34 | 99.3 | yes | 17 | −0.09 | 0 |
| 12435 | F | 29 | 61.1 | yes | 31 | −0.27 | 0 |
| 13520 | F | 36 | 119.6 | yes | 26 | 0.05 | 0 |
| 13522 | F | 30 | 75.2 | yes | 12 | −0.14 | 0 |
| 12450 | F | 30 | 78.8 | yes | 25 | −0.08 | 0 |
| 12406 | F | 31 | 94.5 | yes | 39 | 0.08 | 0 |
| 12366 | F | 29 | 84.0 | yes | 29 | 0.08 | 0 |
| 13610 | M | 26 | 60.4 | yes | 24 | −0.04 | 0 |
| 12402 | F | 26 | 63.7 | yes | 35 | 0.01 | 0 |
| 12409 | F | 36 | 146.0 | yes | 14 | 0.46 | 0 |
| 12381 | F | 26 | 67.5 | yes | 59 | 0.07 | 0 |
| 12438 | F | 30 | 102.3 | yes | 7 | 0.28 | 0 |
| 12454 | F | 36 | 151.6 | yes | 4 | 0.55 | 0 |
| 13533 | M | 24 | 57.3 | yes | 10 | 0.08 | 0 |
| 13511 | F | 35 | 145.9 | No | 72 | 0.54 | 0 |
| 13588 | F | 28 | 91.3 | yes | 3 | 0.28 | 0 |
| 12380 | F | 24 | 60.7 | yes | 21 | 0.13 | 0 |
| 12352 | F | 29 | 101.1 | yes | 46 | 0.35 | 0 |
| 13599 | F | 25 | 70.1 | yes | 15 | 0.20 | 0 |

TABLE 1-continued

Raw data for FIG. 1

| Sample ID | Gender M = Male, F = Female | Age (Years) | anti-P63 IgM units (EU) | Had a relapse event with in follow up time (Yes/No) | Time to next relapse, or time to end of followup (months) | Classifier level | Classifier status: 1 if ≧0.6114674, 0 if <0.6114674 |
|---|---|---|---|---|---|---|---|
| 13540 | M | 26 | 79.4 | yes | 40 | 0.26 | 0 |
| 12322 | F | 31 | 121.4 | yes | 89 | 0.49 | 0 |
| 13512 | F | 30 | 115.8 | yes | 3 | 0.49 | 0 |
| 12457 | F | 29 | 110.3 | yes | 32 | 0.49 | 0 |
| 13605 | F | 26 | 86.8 | yes | 12 | 0.37 | 0 |
| 13516 | F | 30 | 122.0 | yes | 37 | 0.59 | 0 |
| 13612 | F | 29 | 117.9 | yes | 9 | 0.61 | 0 |
| 13653 | F | 22 | 68.0 | yes | 2 | 0.41 | 0 |
| 13524 | F | 26 | 100.3 | yes | 11 | 0.58 | 0 |
| 13554 | F | 31 | 140.7 | yes | 10 | 0.79 | 1 |
| 13618 | F | 33 | 165.0 | yes | 6 | 1.00 | 1 |
| 12314 | F | 27 | 120.2 | yes | 12 | 0.80 | 1 |
| 13593 | F | 24 | 101.9 | yes | 1 | 0.77 | 1 |
| 13531 | F | 28 | 137.6 | yes | 21 | 0.99 | 1 |
| 12449 | F | 25 | 120.5 | yes | 7 | 0.98 | 1 |
| 13601 | F | 24 | 120.3 | yes | 22 | 1.05 | 1 |
| 12426 | F | 23 | 116.6 | yes | 21 | 1.08 | 1 |
| 13506 | F | 26 | 146.3 | yes | 33 | 1.29 | 1 |
| 13541 | F | 20 | 101.8 | yes | 40 | 1.10 | 1 |
| 13596 | F | 20 | 103.4 | yes | 14 | 1.12 | 1 |
| 12388 | F | 22 | 121.1 | yes | 24 | 1.23 | 1 |
| 13622 | F | 21 | 134.4 | yes | 7 | 1.52 | 1 |
| 13535 | F | 37 | 278.6 | yes | 2 | 2.43 | 1 |
| 12419 | F | 20 | 148.9 | yes | 48 | 1.83 | 1 |
| 13598 | F | 22 | 169.4 | yes | 8 | 1.98 | 1 |
| 12367 | F | 22 | 171.4 | yes | 19 | 2.01 | 1 |
| 12346 | F | 22 | 172.1 | yes | 24 | 2.02 | 1 |
| 13582 | M | 21 | 240.8 | yes | 6 | 3.17 | 1 |
| 12401 | F | 46 | 1248.6 | yes | 24 | 16.70 | 1 |

TABLE 2

Final classification rule for prediction of risk for early CDMS based on anti-P63 and age, and its diagnostics performance characteristic (BENEFIT Placebo arm only, n = 109).

| Final Model Classification Rule | Performance Characteristic | Point Estimate | 95% Confidence Interval |
|---|---|---|---|
| logit(p) = 1.170703 − 0.082399 · age + 0.015471 · anti-P63 If p ≧ 0.6114674 then classify patient as 'early relapse'. | Accuracy | 64.00 | [54.59; 73.41] |
| | Sensitivity | 32.61 | [23.42; 41.80] |
| | Specificity | 90.74 | [85.06; 96.42] |
| | PPV | 75.00 | [66.51; 83.49] |
| | NPV | 61.25 | [51.70; 70.80] |

TABLE 3

Kaplan-Meier survival analysis of time to CDMS based on anti P63 and age: data summary (BENEFIT study, Placebo arm only, n = 109).

| Day | classifier 2 | Number at Risk | Number CDMS | Survival | Survival Standard Error |
|---|---|---|---|---|---|
| 0 | <=cut-off 2 | 83 | 0 | 1.0000 | 0 |
| | >cut-off 2 | 26 | 0 | 1.0000 | 0 |
| 90 | <=cut-off 2 | 77 | 4 | 0.9509 | 0.0239 |
| | >cut-off 2 | 23 | 3 | 0.8846 | 0.0627 |
| 180 | <=cut-off 2 | 69 | 11 | 0.8645 | 0.0380 |
| | >cut-off 2 | 22 | 4 | 0.8462 | 0.0708 |
| 270 | <=cut-off 2 | 63 | 17 | 0.7893 | 0.0454 |
| | >cut-off 2 | 21 | 4 | 0.8462 | 0.0708 |
| 360 | <=cut-off 2 | 61 | 19 | 0.7642 | 0.0473 |
| | >cut-off 2 | 16 | 9 | 0.6447 | 0.0953 |
| 450 | <=cut-off 2 | 58 | 22 | 0.7266 | 0.0497 |
| | >cut-off 2 | 15 | 10 | 0.6044 | 0.0975 |
| 540 | <=cut-off 2 | 55 | 24 | 0.7016 | 0.0511 |
| | >cut-off 2 | 10 | 15 | 0.4029 | 0.0982 |
| 630 | <=cut-off 2 | 54 | 24 | 0.7016 | 0.0511 |
| | >cut-off 2 | 6 | 18 | 0.2686 | 0.0911 |
| 720 | <=cut-off 2 | 9 | 27 | 0.6626 | 0.0530 |
| | >cut-off 2 | 3 | 20 | 0.1791 | 0.0797 |
| 810 | <=cut-off 2 | 0 | 27 | — | — |
| | >cut-off 2 | 0 | 20 | — | — |
| 900 | <=cut-off 2 | 0 | 27 | — | — |
| | >cut-off 2 | 0 | 20 | — | — |
| 990 | <=cut-off 2 | 0 | 27 | — | — |
| | >cut-off 2 | 0 | 20 | — | — |
| 1080 | <=cut-off 2 | 0 | 27 | — | — |
| | >cut-off 2 | 0 | 20 | — | — |

TABLE 4

Kaplan-Meier product limit estimates at day 1800 and log rank P-value for comparison between patients positive for classifier versus negative with respect to time to CDMS or McDonalds MS.

| | #events and Kaplan-Meier estimates at day 1800 | | Test result |
|---|---|---|---|
| Time-to-event outcome | N (n = 230) | P, (n = 56) | (p-value) of log-rank test |
| Time to CDMS | 99/53.66% | 35/35.05% | 0.002553 |

TABLE 4-continued

Kaplan-Meier product limit estimates at day 1800 and log rank P-value for comparison between patients positive for classifier versus negative with respect to time to CDMS or McDonalds MS.

| Time-to-event outcome | #events and Kaplan-Meier estimates at day 1800 | | Test result |
|---|---|---|---|
| | N (n = 230) | P, (n = 56) | (p-value) of log-rank test |
| Time to McDonald MS | 181/17.69% | 51/8.93% | 0.048945 |

TABLE 5

Kaplan-Meier survival analysis of time to CDMS based on anti-P63 and age: data summary (BENEFIT study, Placebo and treatment arms, n = 286).

| Day | classifier 1 | Number at Risk | Number CDMS | Survival | Survival Standard Error |
|---|---|---|---|---|---|
| 0 | <=cut-off 1 | 144 | 0 | 1.0000 | 0 |
|  | >cut-off 1 | 36 | 0 | 1.0000 | 0 |
| 90 | <=cut-off 1 | 132 | 10 | 0.9302 | 0.0213 |
|  | >cut-off 1 | 31 | 3 | 0.9126 | 0.0482 |
| 180 | <=cut-off 1 | 122 | 19 | 0.8663 | 0.0286 |
|  | >cut-off 1 | 27 | 6 | 0.8222 | 0.0659 |
| 270 | <=cut-off 1 | 117 | 23 | 0.8379 | 0.0310 |
|  | >cut-off 1 | 24 | 8 | 0.7590 | 0.0745 |
| 360 | <=cut-off 1 | 108 | 30 | 0.7873 | 0.0345 |
|  | >cut-off 1 | 22 | 9 | 0.7273 | 0.0778 |
| 450 | <=cut-off 1 | 103 | 33 | 0.7650 | 0.0358 |
|  | >cut-off 1 | 22 | 9 | 0.7273 | 0.0778 |
| 540 | <=cut-off 1 | 100 | 35 | 0.7502 | 0.0366 |
|  | >cut-off 1 | 22 | 9 | 0.7273 | 0.0778 |
| 630 | <=cut-off 1 | 96 | 38 | 0.7275 | 0.0378 |
|  | >cut-off 1 | 22 | 9 | 0.7273 | 0.0778 |
| 720 | <=cut-off 1 | 88 | 40 | 0.7121 | 0.0385 |
|  | >cut-off 1 | 22 | 9 | 0.7273 | 0.0778 |
| 810 | <=cut-off 1 | 85 | 42 | 0.6960 | 0.0393 |
|  | >cut-off 1 | 20 | 9 | 0.7273 | 0.0778 |
| 900 | <=cut-off 1 | 84 | 43 | 0.6878 | 0.0397 |
|  | >cut-off 1 | 20 | 9 | 0.7273 | 0.0778 |
| 990 | <=cut-off 1 | 81 | 46 | 0.6632 | 0.0407 |
|  | >cut-off 1 | 19 | 10 | 0.6910 | 0.0820 |
| 1080 | <=cut-off 1 | 74 | 52 | 0.6139 | 0.0424 |
|  | >cut-off 1 | 19 | 10 | 0.6910 | 0.0820 |
| 1170 | <=cut-off 1 | 74 | 52 | 0.6139 | 0.0424 |
|  | >cut-off 1 | 19 | 10 | 0.6910 | 0.0820 |
| 1260 | <=cut-off 1 | 73 | 53 | 0.6056 | 0.0426 |
|  | >cut-off 1 | 19 | 10 | 0.6910 | 0.0820 |
| 1350 | <=cut-off 1 | 70 | 54 | 0.5972 | 0.0429 |
|  | >cut-off 1 | 19 | 10 | 0.6910 | 0.0820 |
| 1440 | <=cut-off 1 | 69 | 55 | 0.5886 | 0.0431 |
|  | >cut-off 1 | 17 | 12 | 0.6182 | 0.0880 |
| 1530 | <=cut-off 1 | 65 | 57 | 0.5716 | 0.0435 |
|  | >cut-off 1 | 17 | 12 | 0.6182 | 0.0880 |
| 1620 | <=cut-off 1 | 64 | 58 | 0.5628 | 0.0437 |
|  | >cut-off 1 | 15 | 12 | 0.6182 | 0.0880 |
| 1710 | <=cut-off 1 | 64 | 58 | 0.5628 | 0.0437 |
|  | >cut-off 1 | 15 | 12 | 0.6182 | 0.0880 |
| 1800 | <=cut-off 1 | 49 | 58 | 0.5628 | 0.0437 |
|  | >cut-off 1 | 10 | 12 | 0.6182 | 0.0880 |
| 1890 | <=cut-off 1 | 2 | 58 | 0.5628 | 0.0437 |
|  | >cut-off 1 | 0 | 12 | — | — |
| 1980 | <=cut-off 1 | 1 | 58 | 0.5628 | 0.0437 |
|  | >cut-off 1 | 0 | 12 | — | — |

Figure 4:
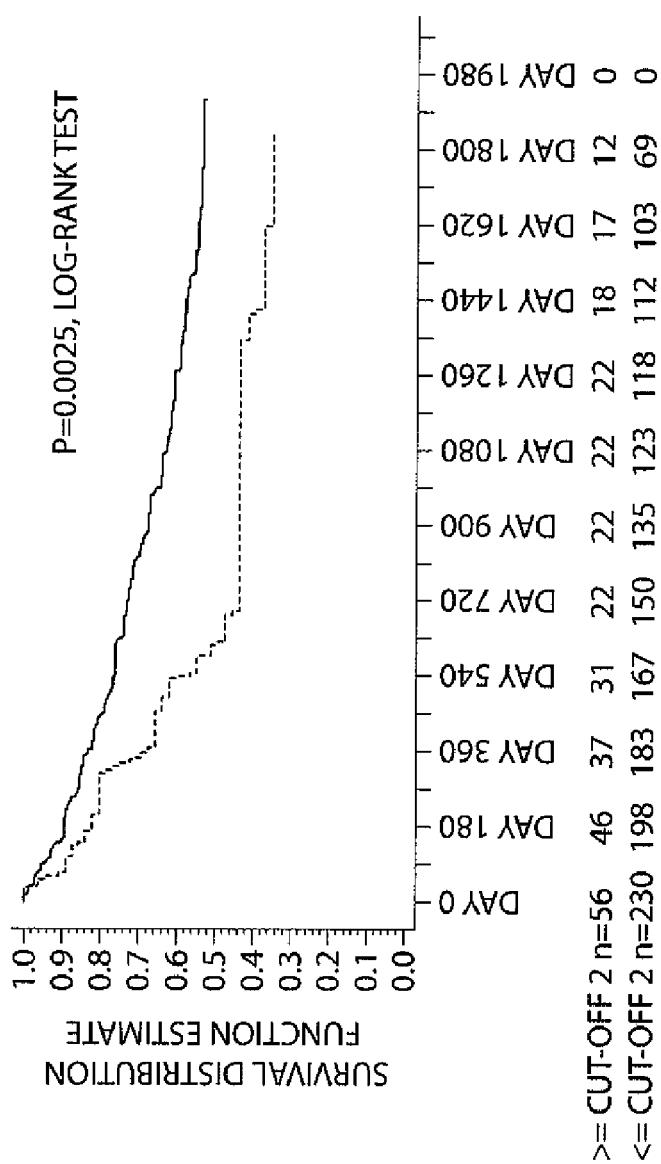
FIG. 4 shows a Kaplan-Meier survival plot for time to CDMS. CIS patient treatment and placebo arms, n=286. Patients were classified as positive (above cutoff, dashed line) or negative (below cutoff, full line) by a classifier based on combination of anti-P63 and age: p=1.170703−0.082399·age (years)+0.015471·anti-P63 (EU). If p≧0.6114674, the patient was classified as positive.
Figure 5:
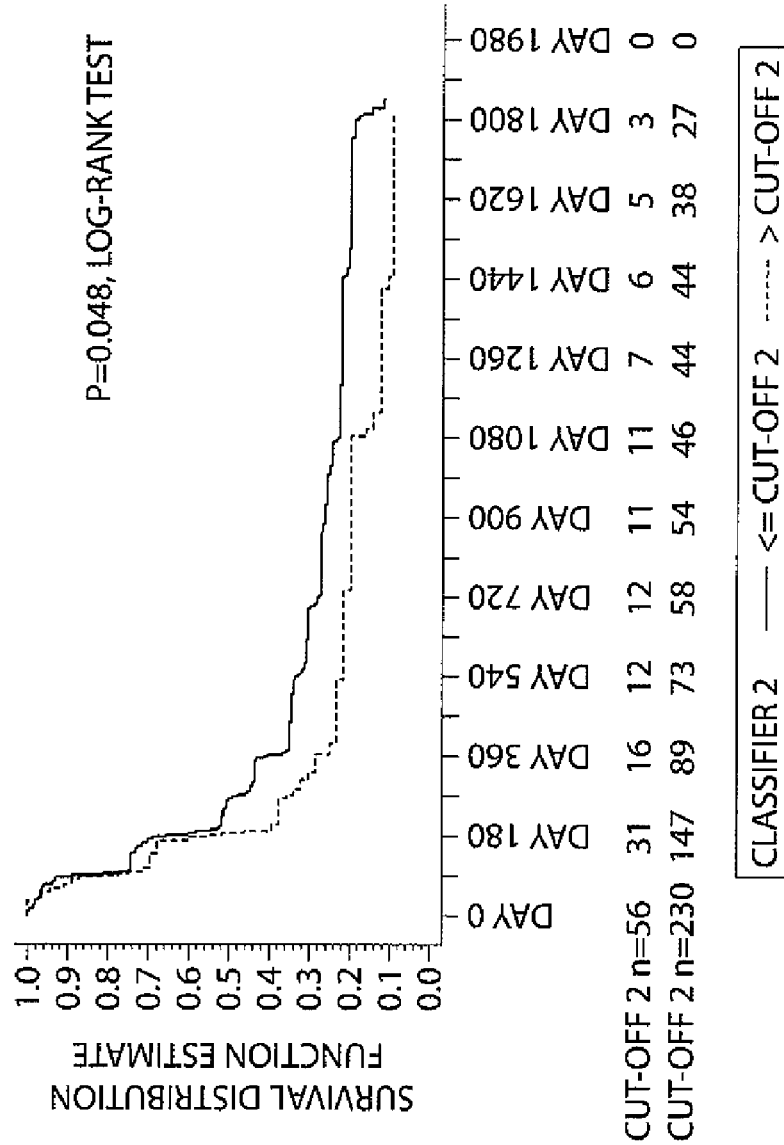
FIG. 5 shows a Kaplan-Meier survival plot for time to McDondals MS. CIS patients treatment and placebo arms, n=286. Patients were classified as positive (above cutoff, dashed line) or negative (below cutoff, full line) by a classifier based on a combination of anti-P63 and age: p=1.170703−0.082399·age (years)+0.015471·anti-P63 (EU). If p≧0.6114674, the patient was classified as positive.

The classifier performance in the full analysis set (placebo and treatment arms, n=286) was examined. 56/286 patients were classified as positive and 230/286 were classified as negative at baseline. At day 1800, the Kaplan-Meier estimate, i.e., the estimated percentage of patients converted to CDMS, of the group that was classified as negative was 53.6% compared to only 35.02% in the group classified as positive (P=0.002, log rank test). See, Tables 4 and 5; and FIG. 4. The estimated percentage of patients that converted to McDonald MS in the group that was classified as negative was 17.7%, compared to only 8.9% in the group classified as positive (P=0.048, log rank test). See, Tables 4 and 6; and FIG. 5.

TABLE 6

Kaplan-Meier survival analysis of time to McDonald MS based on anti P63 and age: data summary (BENEFIT study, Placebo and treatment arms, n = 286).

| Day | classifier 2 | Number at Risk | Number McDonald MS | Survival | Survival Standard Error |
|---|---|---|---|---|---|
| 0 | <=cut-off 2 | 230 | 0 | 1.0000 | 0 |
|  | >cut-off 2 | 56 | 0 | 1.0000 | 0 |
| 90 | <=cut-off 2 | 197 | 29 | 0.8722 | 0.0222 |
|  | >cut-off 2 | 45 | 11 | 0.8036 | 0.0531 |
| 180 | <=cut-off 2 | 147 | 77 | 0.6587 | 0.0316 |
|  | >cut-off 2 | 31 | 25 | 0.5536 | 0.0664 |
| 270 | <=cut-off 2 | 107 | 117 | 0.4794 | 0.0334 |
|  | >cut-off 2 | 20 | 36 | 0.3571 | 0.0640 |
| 360 | <=cut-off 2 | 89 | 134 | 0.4027 | 0.0328 |
|  | >cut-off 2 | 16 | 40 | 0.2857 | 0.0604 |
| 450 | <=cut-off 2 | 76 | 147 | 0.3439 | 0.0318 |
|  | >cut-off 2 | 13 | 43 | 0.2321 | 0.0564 |
| 540 | <=cut-off 2 | 73 | 149 | 0.3348 | 0.0316 |
|  | >cut-off 2 | 12 | 44 | 0.2143 | 0.0548 |
| 630 | <=cut-off 2 | 65 | 156 | 0.3024 | 0.0308 |
|  | >cut-off 2 | 12 | 44 | 0.2143 | 0.0548 |
| 720 | <=cut-off 2 | 58 | 162 | 0.2740 | 0.0300 |
|  | >cut-off 2 | 12 | 44 | 0.2143 | 0.0548 |
| 810 | <=cut-off 2 | 57 | 163 | 0.2693 | 0.0299 |
|  | >cut-off 2 | 11 | 45 | 0.1964 | 0.0531 |
| 900 | <=cut-off 2 | 54 | 165 | 0.2598 | 0.0296 |
|  | >cut-off 2 | 11 | 45 | 0.1964 | 0.0531 |
| 990 | <=cut-off 2 | 52 | 166 | 0.2549 | 0.0294 |
|  | >cut-off 2 | 11 | 45 | 0.1964 | 0.0531 |
| 1080 | <=cut-off 2 | 46 | 171 | 0.2301 | 0.0286 |
|  | >cut-off 2 | 11 | 45 | 0.1964 | 0.0531 |
| 1170 | <=cut-off 2 | 45 | 172 | 0.2251 | 0.0284 |
|  | >cut-off 2 | 7 | 49 | 0.1250 | 0.0442 |
| 1260 | <=cut-off 2 | 44 | 173 | 0.2201 | 0.0282 |
|  | >cut-off 2 | 7 | 49 | 0.1250 | 0.0442 |
| 1350 | <=cut-off 2 | 44 | 173 | 0.2201 | 0.0282 |
|  | >cut-off 2 | 7 | 49 | 0.1250 | 0.0442 |
| 1440 | <=cut-off 2 | 44 | 173 | 0.2201 | 0.0282 |
|  | >cut-off 2 | 6 | 50 | 0.1071 | 0.0413 |
| 1530 | <=cut-off 2 | 38 | 178 | 0.1951 | 0.0271 |
|  | >cut-off 2 | 5 | 51 | 0.0893 | 0.0381 |
| 1620 | <=cut-off 2 | 38 | 178 | 0.1951 | 0.0271 |
|  | >cut-off 2 | 5 | 51 | 0.0893 | 0.0381 |
| 1710 | <=cut-off 2 | 38 | 178 | 0.1951 | 0.0271 |
|  | >cut-off 2 | 5 | 51 | 0.0893 | 0.0381 |
| 1800 | <=cut-off 2 | 27 | 181 | 0.1769 | 0.0266 |
|  | >cut-off 2 | 3 | 51 | 0.0893 | 0.0381 |
| 1890 | <=cut-off 2 | 0 | 185 | — | — |
|  | >cut-off 2 | 0 | 51 | — | — |
| 1980 | <=cut-off 2 | 0 | 185 | — | — |
|  | >cut-off 2 | 0 | 51 | — | — |

A classification rule was developed based on patient age, along with the levels of anti-P63 IgM in patient serum: p=1.170703−0.082399·age (years)+0.015471·anti-P63(EU). If p≧0.6114674, the patient is classified as positive with a risk for early relapse within ≦24 months. Kaplan-Meier survival analysis indicated that patients classified as positive (above cutoff) by the classifier are at higher risk for conversion to CDMS or McDonald MS within 24 months as compared to patients who are negative (below cutoff).

Example 3

BENEFIT Data—Anti-P63 IgM for Prediction of Early CDMS Conversion

The following invention is a method for identification of Clinical isolated syndrome (CIS) patients suggestive of Relapsing Remitting Multiple Sclerosis having higher risk for early conversion to (CDMS). The method is based on measurement of anti-Dextran (glucose based polysaccharide with α1,3 and α1,6 glycosidic bonds (P63)) IgM antibodies level in the sera of a patient. Elevated levels above a certain cutoff indicate a higher risk for early conversion to clinically defined MS (CDMS) in clinical isolated syndrome patients suggestive of relapsing remitting multiple sclerosis.

A prospective analysis was performed on 109 frozen sera samples taken from CIS patients that participated in the BENEFIT study at base line (placebo arm only, untreated patients). The patients were clinically followed-up for 720 days and the conversion to CDMS during this time was recorded. See, the full description of the BENEFIT study in Example 2 above. Levels of anti-Dextran (P63) IgM antibodies in sera samples taken at baseline were measured by enzyme immunoassay (EIA). See, the full description of the sample handling and EIA procedures in Example 2 above. ROC curve analysis of anti-P63 IgM levels for differentiation between patients who convert to CDMS versus patients who did not convert to CDMS during 720 days follow-up period was done by plotting sensitivity (Se(c)) versus 1-specificity (1-Sp(c)) over all possible cutoff values (c). An optimal cut-off level for differentiation between patients who convert to CDMS, versus patients who did not convert to CDMS, was determined at the point of maximal Youden index. This index is defined as $J=\max_c\{Se(c)+Sp(c)-1\}$ and ranges between 0 and 1 (Youden W J, 1950 Cancer, 3: 32-35). Sensitivity, Specificity, NPV and PPV were calculated at this point.

Figure 6:
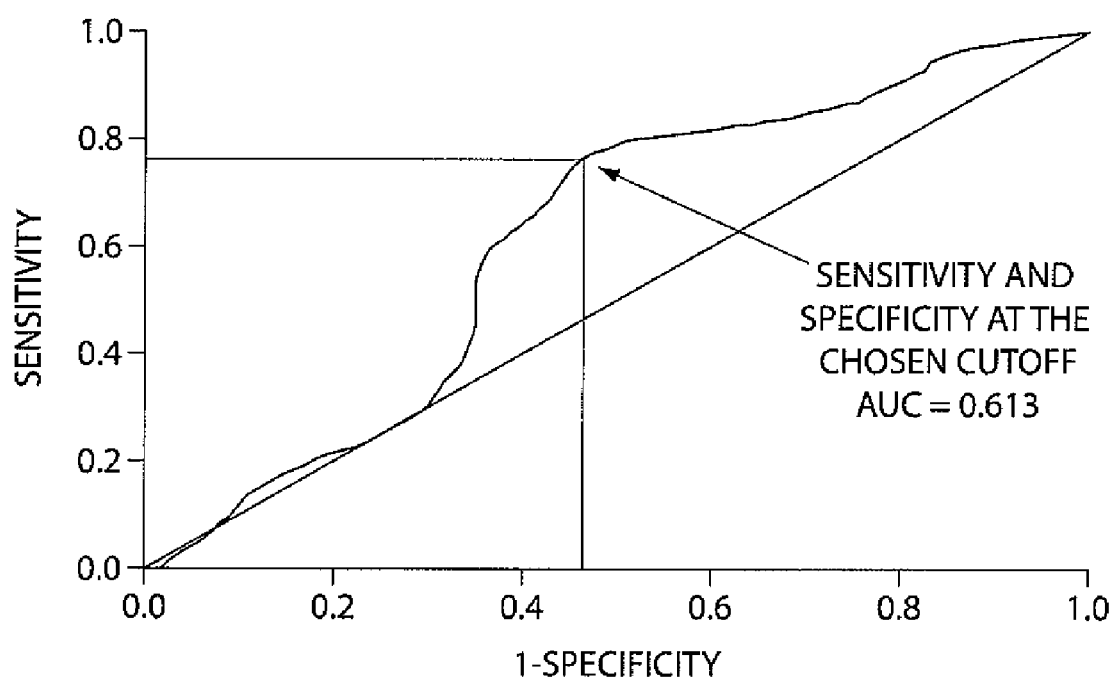
FIG. 6 is an ROC curve, sensitivity versus 1-specificity for all possible cut-off values for differentiation between patients who convert to CDMS within 720 days versus patients who did not convert to CDMS. The sensitivity and 1-specificity at the point of maximal Youden index is marked by arrows. (BENEFIT data, CIS patients Placebo arm, n=109).
Figure 7:
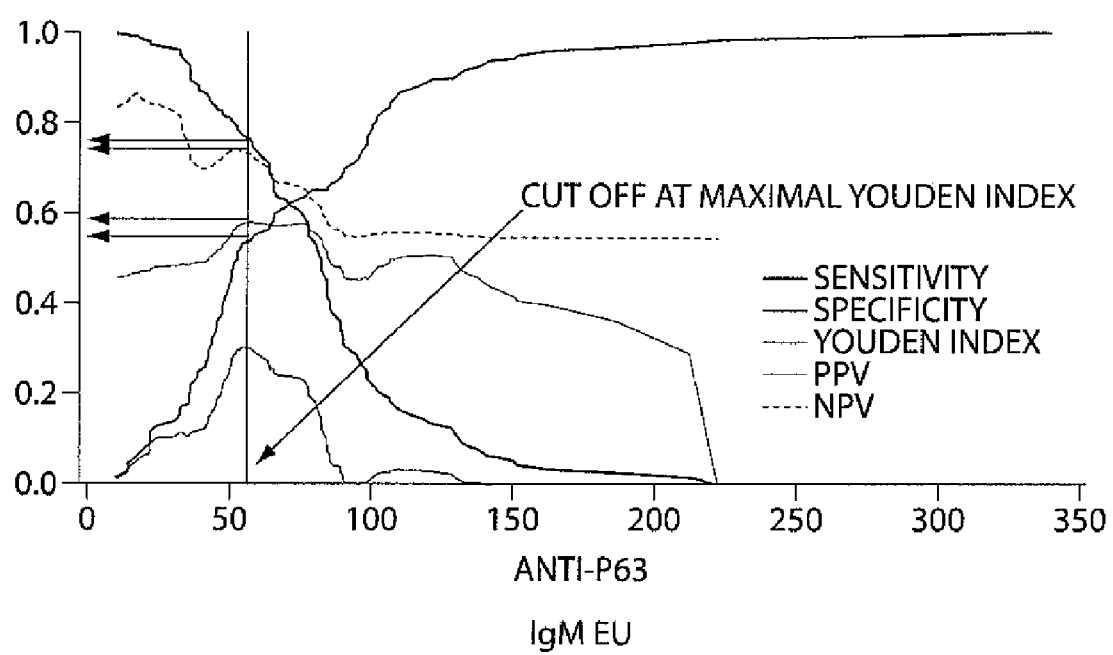
FIG. 7 shows the estimated sensitivity, specificity, Youden index, PPV and NPV depending on anti-P63 level cutoffs for differentiation between patients who convert to CDMS within 720 days versus patients who did not convert to CDMS. (BENEFIT, placebo arm only, n=109).

The Placebo group included 109 CIS patients. 46 out of the 109 patients converted to CDMS during the follow-up period. The area under the curve (AUC) for the ROC curve was 0.67 (FIG. 6). The Maximum Youden index was 0.3. The differentiation between patients who convert to CDMS, versus patients who did not convert to CDMS within 720 days, using a cut-off set to the point of maximum Youden index (at cut-off=54EU) enabled differentiation with a Sensitivity of 76%, a Specificity of 54%, a NPV of 73%, and a PPV of 60%. See, FIG. 7. Thus, an elevated level of anti-P63 IgM (above cutoff) indicates a higher risk for conversion to CDMS with in 24 months, while a lower level (below cut off) indicates a high probability (73%) for not converting to CDMS within 720 days.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a subject with a clinically isolated syndrome (CIS) suggestive of MS who is likely to progress to clinically definitive multiple sclerosis (CDMS) within twenty-four months, the method comprising:
    providing a test sample from said subject;
    detecting in said test sample an anti-Glc (α 1,3) Glc (α) IgM antibody and an anti-Glc (α 1,6) Glc (α) IgM antibody; and
    comparing the levels of said antibodies in said test sample to a control level of said antibodies, wherein a higher level of said antibodies compared to the control level of said antibodies indicates that said subject is likely to progress to CDMS within twenty-four months.

2. The method of claim 1, wherein a higher level of said antibodies in said test sample compared to the control level of said antibodies indicates said subject is at risk of having a second neurological attack within forty-eight months.

3. The method of claim 1, wherein said test sample is whole blood, serum, or plasma.

4. A method of identifying a subject with a clinically isolated syndrome (CIS) suggestive of MS who is likely to progress to clinically definitive multiple sclerosis (CDMS) within twenty-four months, the method comprising:
    providing a test sample from said subject;
    detecting in said test sample IgM antibodies to a polymer comprising Glc (α 1,3) Glc (α) and Glc (α 1,6) Glc (α) disaccharides, wherein said IgM antibodies are detected using said polymer; and
    comparing the levels of said antibodies in said test sample to a control sample level of said antibodies, wherein a higher level of said antibodies compared to the control level of said antibodies indicates that said subject is likely to progress to CDMS within twenty-four months.

5. The method of claim 4, wherein a higher level of said antibodies in said test sample compared to the control level of said antibodies indicates said subject is at risk of having a second neurological attack within forty-eight months.

6. The method of claim 4, wherein said test sample is whole blood, serum, or plasma.

* * * * *